United States Patent [19]

Wittle et al.

[11] 4,086,219

[45] Apr. 25, 1978

[54] NONAPEPTIDES AND METHODS FOR THEIR PRODUCTION

[75] Inventors: Eugene Leroy Wittle; Mildred Catherine Rebstock, both of Ann Arbor, Mich.

[73] Assignee: Parke, Davis & Company, Detroit, Mich.

[21] Appl. No.: 754,785

[22] Filed: Dec. 27, 1976

Related U.S. Application Data

[63] Continuation-in-part of Ser. No. 626,805, Oct. 29, 1975, abandoned.

[51] Int. Cl.$^2$ ............... C07C 103/52; A61K 37/00
[52] U.S. Cl. ............... 260/112.5 LH; 260/112.5 R; 424/177
[58] Field of Search ............... 260/112.5 R, 112.5 LH

[56] References Cited

U.S. PATENT DOCUMENTS 3,914,412  10/1975  Gerdrick et al. ........... 260/112.5 LH
3,937,695  2/1976   Sarantakis ................. 260/112.5 LH
4,016,259  4/1977   Kent, Jr. ................. 260/112.5 R

OTHER PUBLICATIONS

E. Schroeder et al., "The Peptides," I, Academic Press, N.Y., 1965, pp. 22–30, 79–80.

*Primary Examiner*—Delbert R. Phillips
*Attorney, Agent, or Firm*—Stephen Raines; Frank S. Chow; David B. Ehrlinger

[57] ABSTRACT

New nonapeptides having the formula Prot Grp-R-Trp-Ser-Tyr-$R_2$-Leu-Arg-Pro-Gly-$R_3$; salts thereof; wherein R is Gln, Gln (bzl), His (bzl), Ser (bzl), Pro, Leu, Tyr (bzl), Ile, Cys (bzl) or Phe, $R_2$ is D-Phe, D-Ala, D-Leu, D-Trp, D-Tyr, D-Tyr (Me), D-Ser, D-Met, D-Arg, D-Val, D-His, D-Gln, D-Phs, D-Thr, D-Pro or D-Asn and $R_3$ is $NH_2$, NH(lower alkyl) or N-(lower alkyl)$_2$, methods for their production; certain peptide intermediates and their salts used in the production thereof; and the use of said nonapeptides as luteinizing hormone releasing factor antagonists.

9 Claims, No Drawings

NONAPEPTIDES AND METHODS FOR THEIR PRODUCTION

This application is a continuation-in-part application of copending application Ser. No. 626,805, filed Oct. 29, 1975, now abandoned.

SUMMARY AND DETAILED DESCRIPTION

The present invention relates to new peptide compounds that are useful as luteinizing hormone releasing factor antagonists and to methods for their production. More particularly, the invention relates to new nonapeptides that are represented by the formula

Prot Grp-R-Trp-Ser-Tyr-R$_2$-Leu-Arg-Pro-Gly-R$_3$ and to salts thereof, wherein Prot Grp is a protecting group, R is Gln, Gln (bzl), His (bzl), Ser (bzl), Pro, Leu, Tyr (bzl), Ile, Cys (bzl), Phe or Ser (bzl), R$_2$ is D-Phe, D-Ala, D-Leu, D-Trp, D-Tyr, D-Tyr (Me), D-Ser, D-Met, D-Arg, D-Val, D-His, D-Gln, D-Phs, D-Thr, D-Pro or D-Asn and R$_3$ is NH$_2$, NH(lower alkyl) or N(lower alkyl)$_2$, preferably to compounds of the formula

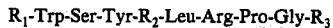

R$_1$-Trp-Ser-Tyr-R$_2$-Leu-Arg-Pro-Gly-R$_3$   I and to salts thereof, wherein R$_1$ is Z-Gln, Z-Gln (bzl), Bhoc-Gln, Boc-His (bzl), Z-His (bzl), Boc-Ser (bzl), Boc-Pro, Z-Leu, Boc-Leu, Z-Tyr (bzl), Z-Ile, Boc-Cys (bzl), Z-Phe or Z-Ser (bzl), R$_2$ is D-Phe, D-Ala, D-Leu, D-Trp, D-Tyr, D-Tyr (Me), D-Ser, D-Met, D-Arg, D-Val, D-His, D-Gln, D-Phs, D-Thr, D-Pro, or D-Asn and R$_3$ is NH$_2$, NH(lower alkyl) or N(lower alkyl)$_2$, with the most preferred compounds being those wherein R$_3$ is NH$_2$; and to certain peptide intermediates and their salts employed in the production thereof. In formula I, the conventional symbols for amino acid residues of peptide compounds and protective groups linked thereto are used and each is intended to have the following meaning: Trp, L-tryptophyl; Ser, L-seryl; Tyr, L-tyrosyl; Leu, L-leucyl; Arg, L-arginyl; Pro, L-prolyl; Gly, glycine; Z-Gln, N$^\alpha$-benzyloxycarbonyl-L-glutaminyl, Z-Gln (bzl), N$^\gamma$-benzyl-N$^\alpha$-benzyloxycarbonyl-L-glutaminyl; Bhoc-Gln, N$^\alpha$-benzhydryloxycarbonyl-L-glutaminyl; Boc-His (bzl), N$^\alpha$-t-butoxycarbonyl-N$^{im}$-benzyl-L-histidyl; Z-His (bzl), N$^\alpha$-benzyloxycarbonyl-N$^{im}$-benzyl-L-histidyl; Boc-Ser (bzl), O-benzyl-N$^\alpha$-t-butoxycarbonyl-L-seryl; Boc-Pro, N$^\alpha$-t-butoxycarbonyl-L-prolyl; Z-Leu, N$^\alpha$-benzyloxycarbonyl-L-leucyl; Boc-Leu, N$^\alpha$-t-butoxycarbonyl-L-leucyl; Z-Tyr (bzl), O-benzyl-N$^\alpha$-benzyloxycarbonyl-L-tyrosyl; Z-Ile, N$^\alpha$-benzyloxycarbonyl-L-isoleucyl; Boc-Cys (bzl), S-benzyl-N$^\alpha$-t-butoxycarbonyl-L-cysteinyl; Z-Phe, N$^\alpha$-benzyloxycarbonyl-L-phenylalanyl; Z-Ser (bzl), O-benzyl-N$^\alpha$-benzyloxycarbonyl-L-seryl; D-Phe, D-phenylalanyl; D-Ala, D-alanyl; D-Leu, D-leucyl; D-Trp, D-tryptophyl; D-Tyr, D-tyrosyl; D-Tyr (Me), O-methyl-D-tyrosyl; D-Ser, D-seryl; D-Met, D-methionyl; D-Arg, D-arginyl; D-Val, D-valyl; D-His, D-histidyl; D-Gln, D-glutaminyl; D-Phs, D-phenylseryl(erythro or threo); D-Thr, D-threonyl; D-pro, D-prolyl; and D-Asn; D-asparaginyl. In addition, the term "protecting group" is intended to mean a group generally used to protect amino groups of peptides, such as benzyloxycarbonyl, t-butoxycarbonyl, substituted benzyloxycarbonyl, etc., other typical groups are shown in E. Schroder and K. Lubke, "The Peptides", Vol. I, Chapter 1., Academic Press, 1966 and J. Meienhofer in "Hormonal Proteins and Peptides", Vol. II, p. 227., Academic Press, 1973, which are incorporated by reference. Lastly, the term "lower alkyl" is intended to mean a straight, branched or cyclic saturated hydrocarbon moiety of up to six carbon atoms, such as methyl, ethyl, isopropyl, and cyclopropyl. The symbols used in the formula I will also be used in the formulae that follow for other compounds and each such symbol should be understood to have the meaning given above.

In accordance with this invention, compounds of the formula I and acid-addition salts thereof are produced by reacting an azide, represented by the formula

X—N$_3$   II with a compound of the formula

Y-Pro-Gly-R$_3$   III in a non-reactive solvent medium, preferably dimethylformamide or a dimethylformamide-tetrahydrofuran mixture wherein X is R$_1$-Trp-Ser-Tyr, R$_1$-Trp-Ser-Tyr-R$_2$ or R$_1$-Trp-Ser-Tyr-R$_2$-Leu, Y is Arg, Leu-Arg or R$_2$-Leu-Arg, and R$_2$ and R$_3$ are as previously defined. The compounds of the formula II and III are selected for reaction so that the resultant product is a nonapeptide of formula I.

The azide of the formula II is prepared and used in situ, while the compound of formula III is used with the Arg group in the form of an acid-addition salt of a strong acid, such as the hydrochloride or trifluoroacetate. The two components, II and III are generally reacted in approximately equimolar amounts at temperatures of from about −30° C to about 30° C for from sixteen to fifty hours, although temperatures of from 30° C to 50° C may be used with a shortened reaction period.

The compounds of formula I are preferably isolated in the form of an acid-addition salt but may if desired be isolated in the form of a free base.

The peptide azide compounds of the formula II that are used as a reactant in the foregoing process are normally prepared in situ by reacting a peptide hydrazide compound represented by the formula

X—NHNH$_2$   IV wherein X is as previously described, with a lower alkyl nitrite, preferably isoamyl nitrite in the presence of an acid in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula IV. The preparation of the azide is carried out at a temperature between −60° and 10° C. Following the in situ formation of the azide of formula II and prior to the further reaction of the peptide azide with the compound of formula III to form the nonapeptide product I, a tertiary amine such as triethylamine is added to the reaction mixture to neutralize the acid used. These azides are also part of the invention.

The peptide hydrazide compounds of formula IV above are prepared by various methods. Certain of these compounds can exist in the form of acid-addition salts, such as the hydrochloride salt, sulfate salt, acetate salt, citrate salt, trifluoroacetate salt, etc., and these salts are included within the invention. The hydrazide of the formula IV, wherein X is as previously described is prepared by reacting an ester of the formula

  X—OR$_4$  V wherein X is as previously defined and R$_4$ is lower alkyl, preferably methyl, with excess hydrazine (1:1.1 to 100) preferably in the form of its hydrate, in an organic solvent, such as dimethylformamide, methanol, ethanol, etc. The reaction is generally carried out at room temperature, although temperatures of from 5° C to 100° C may be employed for periods of from about 30 minutes to about 200 hours, preferably about 72 hours.

The esters of formula V are prepared by reacting a compound of the formula

  X'—OR$_4$  VI wherein R$_4$ is as previously defined and X' is Trp-Ser-Tyr, R$_2$-Leu, Trp-Ser-TYr-R$_2$, Trp-Ser-Tyr-R$_2$-Leu or Leu wherein R$_2$ is as previously defined or a salt of compound VI provided a basic center is present in R$_2$, with a compound having the formula

  X"—OH  VII wherein X" is R$_1$, R$_1$-Trp-Ser-Tyr or R$_1$-Trp-Ser-Tyr-R$_2$ in an organic solvent, such as dimethylformamide. This coupling reaction may be achieved by a number of procedures. Initially it may be conducted at a temperature of about −10° C for 2 hours followed by about 24 hours at room temperature, utilizing compound VII in the form of its pentachlorophenyl ester and triethylamine. A second method which again utilizes dimethylformamide as a solvent and −10° C to 0° C for the first 3 hours, followed by two days at room temperature while relying upon 1-hydroxybenztriazole and dicyclohexylcarbodiimide to promote the reaction. A third procedure involves the conversion of formula VII into its methyl ester by standard esterification reactions, or the ester may be obtained directly from its route of synthesis as described in a subsequent example. The methyl ester is then converted to the corresponding hydrazide according to the procedure given for preparing hydrazides of the formula IV and this material converted to the corresponding azide using the procedure described for the preparation of compounds of the formula II and coupled to compound of the formula VI according to the azide coupling procedures previously described.

By utilizing the above general procedures in the appropriate order, one may build any of the desired esters of the formula V.

Those esters of the formula VI, which are not already reported in the literature, are prepared by the same procedure as given for the preparation of compounds of the formula V, wherein a compound of the formula

  X$^{III}$—OH is combined with a compound of the formula

  X$^{IV}$—OR$_4$ wherein X$^{III}$ is Trp, R$_2$, or Trp-Ser-Tyr, wherein the terminal amino group is protected by a benzyloxycarbonyl, benzhydryloxycarbonyl or t-butoxycarbonyl group, X$^{IV}$ is R$_2$, Leu, R$_2$-Leu, Ser-Tyr or Ser-Tyr-R$_2$-Leu and R$_4$ is as previously defined, followed by removal of benzyloxycarbonyl or benzhydryloxycarbonyl group by dissolving the product in methanol followed by treatment with palladium-on-carbon in the presence of molecular hydrogen for a period of about two and one-half hours at room temperature or removal of the t-butoxycarbonyl group by mild acid decomposition using dilute aqueous acid, such as hydrochloric or trifluoroacetic acid.

All of the compounds of formula X$^{III}$—OH are known compounds in an unprotected form except Trp-Ser-Tyr-OH. While most of the protected compounds are also known, those which do not appear in the literature are prepared by reacting carbobenzoxy chloride or benzhydryloxycarbonyl chloride with the appropriate amino acid in the presence of a base according to the general procedures used in peptide chemistry for introducing protective groups or reacting t-butoxycarbonylazide with the appropriate amino acid according to the procedure described in the text: Solid Phase Peptide Synthesis: J. M. Stewart and J. D. Young, W. H. Freeman & Company, San Francisco (1969), P. 28.

The protected tripeptide is preferably obtained by the earlier described coupling procedures using protected trytophane with Ser-Tyr-OR$_4$, wherein R$_4$ is as previously defined. The Ser-Tyr-OR$_4$ is obtained by deprotecting the carbobenzoxy derivative of Ser-Tyr-OR$_4$.

The compound of the formula X$^{IV}$—OR$_4$ wherein X$^{IV}$ is Leu is reported in the literature and the method for preparing X$^{IV}$—OR$_4$ wherein X$^{IV}$ is Ser-Tyr is given immediately above. Where X$^{IV}$ is Ser-Tyr-R$_2$-Leu, the compound X$^{IV}$—OH is prepared by coupling protected Ser-Tyr-OH to R$_2$-Leu-OR$_4$, wherein R$_2$ and R$_4$ are as previously defined, utilizing the earlier described procedure employing an azide intermediate or coupling the two fragments with the aid of dicyclohexylcarbodiimide in a nonpolar solvent at room temperature until precipitation of dicyclohexyl urea is complete, followed by deprotection using the previously described deprotection procedures. The compounds of the formula R$_2$-Leu-OR$_4$ are prepared by coupling the protected known compound R$_2$—OH with known Leu-OR$_4$ using the above described azide or dicyclohexylcarbodiimide procedures and previously described deprotection procedures. Where X$_4$ is R$_2$ standard esterification procedures are employed.

The compounds of the formula VII, which are not already reported in the literature or described in another portion of this specification are prepared by essentially the same procedure as given for the preparation of compounds of the formula V. A compound of the formula

  X$^V$—OH is combined with a compound of the formula

  X$^{VI}$—OR$_4$ wherein X$^V$ is R$_1$-Trp-Ser-Tyr and X$^{VI}$ is R$_2$ using the procedure described for the preparation of compounds of the formula V. Hydrolysis of the resulting esters using dilute alkali in only slightly more than equimolar amounts yields the free acid of formula VII, or the ester may be used via the hydrazide and azide procedures as described elsewhere for directly preparing the compound of formula V.

The compounds of the formula $X^{II}OH$ wherein $X^{II}$ is $R_1$ are all known, except Bhoc-Gln which is prepared from benzhydryloxycarbonyl hydrazide, sodium nitrite and L-glutamine using aqueous acetic acid as the solvent and a temperature of 5° C. The compounds of the formula $X^V OH$ wherein $X^V$ is $R_1$-Trp-Ser-Tyr are prepared by reacting a known $R_1$—OH compound with the tripeptide Trp-Ser-Tyr-OR$_4$ according to the procedure described for the preparation of compounds of the formula V, followed by hydrolysis of the ester, or the ester may be used via the hydrazide and azide coupling procedure as described elsewhere for directly preparing the compound of formula VII.

The compounds of the formula $X^{VI}OR_4$ are prepared from known D-amino acids by standard esterification techniques.

The compounds for the formula III and their acid-addition salts, such as hydrochloride salt, sulfate salt, acetate salt, citrate salt, trifluoroacetate salt, benzoate salt, etc., are prepared by various methods. The novel compounds of formula III and their acid-addition salts, which are also part of this invention, are those wherein Y is Y' and Y' is defined as $R_2$-Leu-Arg. Compounds of the formula III and their acid-addition salts wherein Y, $R_2$ and $R_3$ are as previously described, are prepared by reducing the protective group off, or removing a protective group by acid decomposition from a compound of the formula Y"-Pro-Gly-R$_3$  VIII preferably in the form of its acid-addition salt wherein $R_3$ is as previously defined and Y" is Arg, Leu-Arg or preferably $R_2$-Leu-Arg, wherein the terminal amino group is protected by a group that is readily removed by reduction, such as benzyloxycarbonyl or benzhydryloxycarbonyl, wherein the compound is dissolved in a solvent such as lower alkyl alcohol, preferably methanol, using a noble metal catalyst such as palladium-on-carbon in the presence of molecular hydrogen or by cleavage when the protective group is readily removed by acid decomposition such as t-butoxycarbonyl, utilizing an acid such as trifluoroacetic acid, hydrochloric acid, hydrobromic acid, etc., in an appropriate solvent system, such as dioxane, dichloromethane, acetic acid, etc. The reduction or acid decomposition reactions are conducted at from about 10° C to about 50° C, preferably room temperature, for periods of from a few minutes to about 8 hours, preferably about 15 minutes for the acid decomposition reaction. The pH may be adjusted so as to convert the compound to its free base.

The salts of the compounds of formula VIII are prepared from the methyl esters of the formula Y"-Pro-Gly-OCH$_3$.HCl  IX wherein Y" is as previously described, which is reacted with a compound selected from the group consisting of ammonia, lower alkylamine or di(lower alkyl)amine. The reactions are conducted at temperatures of from about 5° C to about 60° C for from a few hours to about 10 days. When employing highly volatile amines, the reaction is conducted in a sealed pressure apparatus.

It is also sometimes advantageous when $R_3H$ is less reactive to prepare compounds of formula III starting with P-Pro-Gly-R$_3$ (IIIa) where P is a suitable protecting group such as benzyloxycarbonyl or t-butyloxycarbonyl. After the removal of the protecting group from P-Pro-Gly-R$_3$ by methods described above, the resulting Pro-Gly-R$_3$ can then be coupled to Y'"—OH by standard peptide procedures such as dicyclohexylcarbodiimide in t-butanol. Removal of the protecting group of the resulting Y"-Pro-Gly-R$_3$ then yields the desired compound of the formula III (Y-Pro-Gly-R$_3$).

The preparation of P-Pro-Gly-R$_3$ can be achieved by a variety of methods including the reaction of R$_3$H with P-Pro-Gly-OH after the latter compound is converted to an activated intermediate via dicyclohexylcarbodiimide, dicyclohexylcarbodiimide in combination with pentachlorophenol, with diphenylphosporyl azide (Chem. Pharm. Bull. (Tokyo) 22, 859-63, 1974) or by the mixed anhydride method.

The compounds of the formula IX are prepared from known Pro-Gly-OCH$_3$.HCl which is coupled to known protected Arg-OH, protected Leu-Arg-OH or protected R$_2$-Leu-Arg-OH according to the procedure given for the preparation of compounds of the formula V. A second procedure for preparing certain compounds of the formula IX involves the coupling of Arg-Pro-Gly-OCH$_3$.HCl with known protected Leu-OH or protected R$_2$-Leu-OH.

In addition, compounds of the formula VIII may be prepared by reacting protected Pro-Gly-OR$_4$ with an amine of the formula R$_3$H, wherein R$_3$ is as previously described, utilizing the reaction conditions given for the preparation of compounds of the formula VIII. The resultant product, protected Pro-Gly-R$_3$ is deprotected by the procedures given for the removal of a protective group from a compound of the formula VIII. The compounds of the formula Pro-Gly-R$_3$ are coupled to either known protected Arg-OH or protected Leu-Arg-OH according to the procedure given for the preparation of compounds of the formula V.

Lastly, the amide function may be introduced into a free acid of the formula

Y"-Pro-Gly-OH wherein Y" is as previously defined utilizing the general procedure described for preparing certain of the compounds of the formula VIII, and the resulting compound of the formula Y"-Pro-Gly-R$_3$ is deprotected as previously described in the preparation of compounds of the formula III.

Alternatively, compounds of the formula III may be prepared by stepwise coupling and deprotecting of a compound of the formula Y"'-Pro-R$_3$ using protected Leu-OH, protected Arg-OH, protected Leu-Arg-OH, protected R$_2$-OH, in the appropriate number and order, according to the procedure given for the preparation of compounds of the formula V.

The compounds of this invention form acid-addition salts with any of a variety of inorganic and organic acids. Pharmaceutically-acceptable acid-addition salts are formed with such acids as hydrochloric, hydrobromic, sulfuric, phosphoric, acetic, succinic, citric, maleic, malic, gluconic, pamoic and related acids. The invention includes acid-addition salts generally as any toxic salt can be converted to the free base or to a pharmaceutically-acceptable salt. The free base and the acid-addition salt forms are interconvertible by adjustment of the pH or by the use of ion-exchange resins. They may differ in solubility properties, but except as noted above are otherwise equivalent for purpose of the invention.

In addition, the compounds of this invention and their release in the female rat and LRF-induced ovulation in the rabbit.

Following are the results of the above in vitro tests on certain preferred compounds.

ACTIVITY TABLE FOR IN VITRO TEST IN RAT ANTERIOR PITUITARY CELL CULTURES

| Compound | Molar Conc. | LH Value ng/ml. | % LH Release Inhibition |
|---|---|---|---|
| $N^\alpha$-Benzyloxycarbonyl-O- | $6 \times 10^{-9}$ | 4.59 | 109 |
| benzyl-L-seryl-L-tryp- | $3.5 \times 10^{-9}$ | 6.96 | 99 |
| tophyl-L-seryl-L-tyrosyl- | $2 \times 10^{-9}$ | 9.84 | 88 |
| D-phenylalanyl-L-leucyl- | $1 \times 10^{-9}$ | 17.85 | 56 |
| L-arginyl-L-prolyl- | $6 \times 10^{-10}$ | 18.89 | 52 |
| glycinamide hydrochloride | $3.5 \times 10^{-10}$ | 23.09 | 36 |
|  | $2 \times 10^{-10}$ | 28.47 | 14 |
|  | $1 \times 10^{-10}$ | 34.50 | 0 |
| LRF Control | $3.5 \times 10^{-10}$ | 32.11 |  |
| Saline Control |  | 6.76 |  |
| $N^\alpha$-Benzyloxycarbonyl-L- | $7 \times 10^{-8}$ | 9.49 | 93 |
| glutaminyl-L-tryptophyl- | $4 \times 10^{-8}$ | 9.79 | 91 |
| L-seryl-L-tyrosyl-D- | $2 \times 10^{-8}$ | 10.07 | 90 |
| phenylalanyl-L-leucyl-L- | $1.2 \times 10^{-8}$ | 13.47 | 71 |
| arginyl-L-prolyl-glycin- | $7 \times 10^{-9}$ | 18.60 | 42 |
| amide acetic acid salt | $4 \times 10^{-9}$ | 20.76 | 30 |
|  | $2 \times 10^{-9}$ | 22.43 | 21 |
| LRF Control | $3.5 \times 10^{-10}$ | 26.23 |  |
| Saline Control |  | 8.24 |  |
| $N^\alpha$-t-Butoxycarbonyl-O- | $6 \times 10^{-8}$ | 7.80 | 108 |
| benzyl-L-seryl-L-trypto- | $2.5 \times 10^{-8}$ | 8.95 | 104 |
| phyl-L-seryl-L-tyrosyl-D- | $1 \times 10^{-8}$ | 8.96 | 104 |
| tryptophyl-L-leucyl-L- | $6 \times 10^{-9}$ | 10.64 | 99 |
| arginyl-L-prolyl-glycin- | $2.5 \times 10^{-9}$ | 18.85 | 72 |
| amide hydrochloride | $1 \times 10^{-9}$ | 21.44 | 64 |
|  | $6 \times 10^{-10}$ | 25.53 | 50 |
|  | $2.5 \times 10^{-10}$ | 29.05 | 39 |
| LRF Control | $3.5 \times 10^{-10}$ | 40.92 |  |
| Saline Control |  | 10.27 |  |
| $N^\alpha$-p-Methoxybenzyloxycarbonyl- | $1 \times 10^{-7}$ | 18.59 | 99 |
| O-benzyl-L-seryl-L-tryptophyl- | $1 \times 10^{-8}$ | 15.95 | 105 |
| L-seryl-L-tyrosyl-D-phenyl- |  |  |  |
| alanyl-L-leucyl-L-arginyl-L- |  |  |  |
| prolyl-glycinamide |  |  |  |
| LRF Control | $(5 \times 10^{-10})$ | 71.56 |  |
| Saline Control |  | 18.29 |  |
|  | $1 \times 10^{-8}$ | 16.01 | 88 |
|  | $1 \times 10^{-9}$ | 32.94 | 41 |
|  | $5 \times 10^{-10}$ | 28.95 | 52 |
|  | $2.5 \times 10^{-10}$ | 34.87 | 35 |
| LRF Control | $(5 \times 10^{-10})$ | 47.31 |  |
| Saline Control |  | 11.81 |  |
| $N^\alpha$-Benzyloxycarbonyl-L-isoleucyl- | $1 \times 10^{-5}$ | 20.69 | 96 |
| L-tryptophyl-L-seryl-L-tyrosyl- | $1 \times 10^{-6}$ | 20.24 | 96 |
| D-tryptophyl-L-leucyl-L-arginyl- | $1 \times 10^{-7}$ | 20.50 | 96 |
| L-prolyl-glycinamide | $1 \times 10^{-8}$ | 21.04 | 95 |
| LRF Control | $(5 \times 10^{-10})$ | 71.56 |  |
| Saline Control |  | 18.29 |  |
|  | $1 \times 10^{-8}$ | 14.00 | 98 |
|  | $5 \times 10^{-9}$ | 18.49 | 87 |
|  | $2.5 \times 10^{-9}$ | 24.96 | 70 |
|  | $1 \times 10^{-9}$ | 36.46 | 41 |
| LRF Control | $(5 \times 10^{-10})$ | 52.80 |  |
| Saline Control |  | 13.28 |  | acid-addition salts can exist in anhydrous forms as well as in solvated, including hydrated, forms. In general, the hydrated forms and the solvated forms with pharmaceutically-acceptable solvents are equivalent to the anhydrous or unsolvated form for the purpose of the invention. Typical hydrates would be the aforementioned hydrochlorides or sulfates in the form of their monohydrates.

The compounds of this invention may be found in mixtures containing its stereoisomers.

Nonapeptides of this invention are screened for LRF antagonist activity in vitro using rat anterior pituitary cell cultures as described by Vale et al. [Endocrinology, 91, 562 (1972)]. The inhibition of LRF-induced luteinizing hormone (LH) release into the culture medium is the endpoint in this in vitro bioassay. Active peptides are then tested in vivo by the procedures of Humphrey et al. [Endocrinology, 92, 1515 (1972)]. Antagonist activity is asessed by the inhibition of LRF-induced LH release in the female rat and LRF-induced ovulation in the rabbit.

The luteinizing hormone releasing factor (LRF) is known to be formed in the hypothalamus of mammals, from which it is released and transported by way of the hypothalamic-hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. (For a report of the structure of LRF, which has also been referred to as luteinizing hormone releasing hormone, or LH-RH, and its biological activity, see Science, Vol. 174, No. 4008, Oct. 29, 1971, pages 511-512.) Thus, the nonapeptides of this invention are useful in controlling ovulation and in restricting fertility.

The invention is illustrated by the following examples.

EXAMPLE 1

$N^\alpha$-BENZYLOXYCARBONYL-O-BENZYL-L-SERYL-L-TRYPTOPHYL-L-SERYL-L-TYROSYL-D-PHENYLALANYL-L-LEUCYL-L-ARGINYL-L-PROLYLGLYCINAMIDE HYDROCHLORIDE

(a) $N^\alpha$-Benzyloxycarbonyl-L-tryptophyl-L-serine methyl ester

L-Serine methyl ester hydrochloride, 5 g., is dissolved in 75 ml. of dimethylformamide and the solution cooled in an ice bath. Triethylamine, 4.9 ml., is added then 11.9 g. of $N^\alpha$-benzyloxycarbonyl-L-tryptophan, 5.25 g. of 1-hydroxybenztriazole and finally 8.0 g of dicyclohexylcarbodiimide. The reaction is stirred with ice bath cooling overnight, allowing the temperature to rise to room temperature, then an additional twenty-four hours at room temperature. The mixture is filtered and the solid washed with dimethylformamide. The filtrate is evaporated under reduced pressure and the residue dissolved in ethyl acetate and washed with dilute hydrochloric acid, saturated salt solution, three times with 5% sodium bicarbonate solution, saturated salt solution, and finally with water. The ethyl acetate solution is then dried over magnesium sulfate and evaporated. The residue is crystallized from 250 ml. of benzene and then from ethyl acetate and petroleum ether; 12.5 g.; m.p. 133°–135° C.; $[\alpha]_D^{23} -12.4°$ (c 2, methanol); ultraviolet in methanol $\lambda_{max}$ 290 $E_1^1$ 115; $\lambda_{max}$ 281 $E_1^1$ 131; $\lambda_{max}$ 274 $E_1^1$ 122.

(b) $N^\alpha$-Benzyloxycarbonyl-L-tryptophyl-L-seryl hydrazide

The methyl ester, 12.3 g., is dissolved in 180 ml. of methanol and treated with 8 ml. of hydrazine hydrate. The reaction is let stand at room temperature overnight and is filtered. The solid product is washed with cold methanol, boiled with 400 ml. of methanol and filtered hot; 8.33 g.; m.p. 176°–178° C.; $[\alpha]_D^{23} -18°$ (c 2.2, DMF); ultraviolet in methanol $\lambda_{max}$ 290 $E_1^1$ 117; $\lambda_{max}$ 281 $E_1^1$ 134; $\lambda_{max}$ 274 $E_1^1$ 125.

(c) $N^\alpha$-Benzyloxycarbonyl-L-tryptophyl-L-seryl-L-tyrosine methyl ester $N^\alpha$-Benzyloxycarbonyl-L-tryptophyl-L-seryl hydrazide, 9.9 g. (22.5 mmol) is dissolved in 150 ml. of spectro grade dimethylformamide and cooled to −20° C. The cold solution is treated with 51 ml. of 2.34N hydrogen chloride in tetrahydrofuran and with 4.7 ml. of isopentylnitrite (90%) and is stirred at −20° C. for one-half hour. The solution is then cooled to −25° C. and treated with 20.45 ml. of triethylamine and with 5.74 g. of L-tyrosine methyl ester hydrochloride. The reaction is stirred at −20° C. for one-half hour, at −20° to −10° C. for 15 minutes and at 0° C. for 3 hours. The mixture is then stored at 0 to 5° C. overnight and is filtered. The solvents are removed under reduced pressure. The residue is dissolved in ethyl acetate and washed with 0.1N hydrochloric acid, saturated salt solution, 5% sodium bicarbonate solution and saturated salt solution. The ethyl acetate is dried and evaporated. The residue is taken into ethanol and crystallization achieved by cooling and scratching during 48 hours. The product is separated on a funnel and washed with ethanol; 8 g. $[\alpha]_D^{25} -5.8°$ (c 1.04, DMF); ultraviolet in methanol $\lambda_{max}$ 290 $E_1^1$ 94.4; $\lambda_{max}$ 279 $E_1^1$ 124. The ethanol liquors yield a second crop of 1.95 g.

(d) $N^\alpha$-Benzyloxycarbonyl-L-tryptophyl-L-seryl-L-tyrosyl hydrazide

The methyl ester, 4.5 g., is dissolved in 50 ml. of methanol and treated with 4.5 ml. of hydrazine hydrate. The reaction is let stand at room temperature for 48 hours. The precipitated product is separated by filtration and washed with methanol. The damp solid is suspended in 150 ml. of ether for two hours and filtered; 4.18 g.; m.p. 226°–229° C.; $[\alpha]_D^{23} -15.6°$ C. (c 1.01, DMF); ultraviolet in methanol $\lambda_{max}$ 289.5 $E_1^1$ 92.6; $\lambda_{max}$ 280 $E_1^1$ 122.

(e) $N^\alpha$-Benzyloxycarbonyl-D-phenylalanyl-L-leucine methyl ester

A solution of 6.65 g. of $N^\alpha$-benzyloxycarbonyl-D-phenylalanine (0.022 mol) and 4.38 g. (0.022 mol) of L-leucine methyl ester hydrochloride in 60 ml. of spectrograde dimethylformamide is chilled in ice and treated with 3.0 ml. of triethylamine (2.24 g.). 1-Hydroxybenztriazole, 3.3 g., and dicyclohexylcarbodiimide, 5 g., are added and the reaction stirred to room temperature overnight and for 24 hours at room temperature. The mixture is filtered and the solvent evaporated under reduced pressure. The residue is dissolved in 200 ml. of ethyl acetate and washed with 0.1N hydrochloric acid, saturated salt solution, 5% sodium bicarbonate solution, saturated salt solution and water. The ethyl acetate solution is dried over magnesium sulfate, filtered and evaporated to a crystalline residue. The product is recrystallized twice from ethyl acetate and petroleum ether; 7.3 g.; m.p. 125°–126° C.; $[\alpha]_D^{23} -20.3°$ (c 1.02, methanol).

(f) D-Phenylalanyl-L-leucine methyl ester hydrochloride

A solution of 7 g. (0.016 mol) of $N^\alpha$-benzyloxycarbonyl-D-phenylalanyl-L-leucine methyl ester in 120 ml. of methanol is treated with 6.12 ml. of 2.68N hydrogen chloride in methanol and reduced with hydrogen and 500 mg. of 10% palladium-on-carbon at atmospheric pressure. The reaction is monitored by thin layer chromatography. The mixture is filtered to separate the catalyst and the solution evaporated; 5.4 g. as a glass; $[\alpha]_D^{23} -82.5°$ (c 1.02, methanol).

(g) $N^\alpha$-Benzyloxycarbonyl-L-tryptophyl-L-seryl-L-tyrosyl-D-phenylalanyl-L-leucine methyl ester A solution of 8.5 g. (0.014 mol) of $N^\alpha$-benzyloxycarbonyl-L-tryptophyl-L-seryl-L-tyrosyl hydrazide in 150 ml. of dimethylformamide is chilled to −20° C. and treated with 34.4 ml. of 2.56N hydrogen chloride in tetrahydrofuran followed by 2.68 ml. of isopentylnitrite. The mixture is stirred at −20° C. for one-half hour, cooled to −25° C., treated with 13.73 ml. of triethylamine and 4.90 g. of D-phenylalanyl-L-leucine methyl ester hydrochloride added. The mixture is stirred at −20° C. for 30 minutes, at −20° to −10° C. for 15 minutes, for 3 hours in salt-ice and overnight at 0° to 5° C. The reaction mixture is filtered on sintered glass and the filtrate evaporated under reduced pressure. The residue is dissolved in ethyl acetate and washed with 0.5N hydrochloric acid, saturated salt solution, 5% sodium bicarbonate solution, saturated salt solution and finally with water. The solution is dried over magnesium sulfate, filtered and the solvent evaporated. The residue is crystallized from 125 ml. of methanol. The product is suspended in 200 ml. of ether for 2 hours, filtered and dried; 6.25 g.; m.p. 221°–223° C.; $[\alpha]_D^{23}$ −21° (c 1.01, DMF); ultraviolet in methanol $\lambda_{max}$ 289.5 $E_1^1$ 66.5; $\lambda_{max}$ 280 $E_1^1$ 86.5.

(h)

L-Tryptophyl-L-seryl-L-tyrosyl-D-phenylalanyl-L-leucine methyl ester $N^\alpha$-benzyloxycarbonyl-L-tryptophyl-L-seryl-L-tyrosyl-D-Phenylalanyl-L-leucine methyl ester, 6.0 g., is dissolved in 140 ml. of absolute methanol and 800 mg. of 20% palladium-on-carbon added. The mixture is reduced under a hydrogen atmosphere, monitoring by thin layer chromatography. The catalyst is removed by filtration using a filter aid (Super-Cel). The solvent is evaporated to leave a solid residue which is dried under reduced pressure and used without further treatment.

(i)

$N^\alpha$-Benzyloxycarbonyl-O-benzyl-L-seryl-L-tryptophyl-L-seryl-L-tyrosyl-D-phenylalanyl-L-leucine methyl ester L-Tryptophyl-L-seryl-L-tyrosyl-D-phenylalanyl-L-leucyl methyl ester, 1.53 g., is dissolved in 35 ml. of dimethylformamide and the solution cooled in ice. $N^\alpha$-Benzyloxycarbonyl-O-benzyl-L-serine, 691 mg., is added with 311 mg. of 1-hydroxybenztriazole and 475 mg. of dicyclohexylcarbodiimide. The reaction is stirred overnight to room temperature and twenty-four hours additionally at room temperature. The mixture is filtered and the filtrate evaporated under reduced pressure. The residue is dissolved in 500 ml. of ethyl acetate and washed with 0.5N hydrochloric acid, saturated salt solution, 5% sodium bicarbonate, saturated salt solution, and finally water. The solution is dried over magnesium sulfate and evaporated. The residue is dried under reduced pressure; 1.92 g.; $[\alpha]_D^{23}$ −13.2° (c 1.03, DMF); ultraviolet in methanol $\lambda_{max}$ 289.5 $E_1^1$ 52.5; $\lambda_{max}$ 280 $E_1^1$ 69.

(j)

$N^\alpha$-Benzyloxycarbonyl-O-benzyl-L-seryl-L-tryptophyl-L-seryl-L-tyrosyl-D-phenylalanyl-L-leucyl hydrazide $N^\alpha$-Benzyloxycarbonyl-O-benzyl-L-seryl-L-tryptophyl-L-seryl-L-tyrosyl-D-phenylalanyl-L-leucine methyl ester, 1.75 g., is dissolved in 40 ml. of dimethylformamide and treated with 2.5 ml. of hydrazine hydrate. After 2.5 hours at room temperature. 15 ml. of methanol is added and the reaction continued overnight at room temperature. The methanol is removed by evaporation and the solution diluted with 80 ml. of isopropanol. The reaction is let stand overnight at room temperature and the precipitate separated by filtration, triturated with ether and dried under reduced pressure; 1.3 g.; m.p. 240°–242° C. dec; $[\alpha]_D^{23}$ −31.2° (c 0.895, DMF); ultraviolet in methanol $\lambda_{max}$ 290 $E_1^1$ 52.5; $\lambda_{max}$ 280 $E_1^1$ 68.7.

(k) $N^\alpha$-Benzyloxycarbonyl-L-prolyl-glycinamide $N^\alpha$-Benzyloxycarbonyl-L-proline, 64.2 g., is dissolved in 350 ml. of dichloromethane, cooled to −10° C. and treated with 41.2 ml. of triethylamine and then with 32.4 g. of ethyl chloroformate with stirring. After 20 minutes at −10° C., a solution of 42 g. of glycine ethyl ester hydrochloride and 41.2 ml. of triethylamine in 250 ml. of dichloromethane is added at −10° C. The reaction is stirred at −10° C. for 1 hour, at −5° C. for 1 hour, at 5° C. for 1 hour and at 25° C. for 20 hours. Water, 100 ml., is added and the dichloromethane is separated, washed twice with 5 percent sodium bicarbonate solution (100 ml. each), with water (100 ml.), twice with dilute hydrochloric acid (30 ml. each), with water (100 ml.) and dried over magnesium sulfate. The solution is filtered and evaporated at 50° C. under reduced pressure to an oil. The oil is dissolved in 100 ml. of methanol, added at 0° C. to 10° C. to 500 ml. of methanol saturated with ammonia at 10° C. and kept at 0° C. for 20 hours, at 25° C. for 6 hours and again at 0° C. for 20 hours. The solution is evaporated under reduced pressure to a small volume where crystallization is started. While the solid is still wet with methanol, 100 ml. of tetrahydrofuran is added and the mixture warmed gently to partially dissolve the solid. The mixture is cooled in ice and, after four hours is filtered and the solid is air-dried to give 59 g.; m.p. 142°–145° C.; $[\alpha]_D^{23}$ −32.1° (C. 2, DMF).

(l) L-Prolyl-glycinamide

A solution of 15.3 g. of $N^\alpha$-benzyloxycarbonyl-L-prolyl-glycinamide in 150 ml. of methanol is shaken with 150 mg. of 20 percent plladium-on-carbon under hydrogen gas at three atmospheres pressure for forty-five minutes. The catalyst is removed by filtration using a filter aid and rinsing with methanol. The filtrate is evaporated to dryness at 40° C. under reduced pressure. The crystalline solid remaining is dried further at 45° C. and reduced pressure and is suitable for use without further purification.

(m)

$N^\alpha$-Benzyloxycarbonyl-L-arginyl-L-prolyl-glycinamide hydrochloride

L-Prolyl-glycinamide (obtained by de-protection of 15.3 g. of $N^\alpha$-benzyloxycarbonyl-L-prolyl-glycinamide), 15.4 g. of $N^\alpha$-benzyloxycarbonyl-L-arginine, 7.4 g. of 1-hydroxybenztriazole and 200 ml. of dimethylformamide are stirred and cooled to −10° C. Hydrogen chloride in tetrahydrofuran, 19.4 ml. of 2.58N, is added and the mixture stirred at −10° C. to 40° C. until solution is complete. The solution is cooled to −30° C. and 11 g of N,N'-dicyclohexylcarbodiimide and 20 ml. of dimethylformamide is added. The solution is stirred at −20° C. to 0° C. for 3 hours, at 20° C. for 16 hours, and at 45° C. for 1 hour. The solution is cooled to 20° C., filtered, the solid rinsed with 20 ml. of methanol and the filtrate evaporated to dryness at 40° C. under reduced pressure. The residue is stirred in 200 ml. of water at 30° C., then cooled in an ice bath and the insoluble solid filtered off and washed twice with 10 ml. of water each time. The filtrate is put over a column (2.5×40 cm) of Dowex 1×2 ion exchange resin (chloride form) to remove 1-hydroxybenztriazole and the eluate is lyophilized to a foam. The foam is dissolved in 35 ml. of methanol and 70 ml. of chloroform and is chromatographed over a column of 350 g. of silica gel (3.7×70 cm), eluting with chloroform:methanol (2:1). The desired fractions as shown by thin layer chromatography are combined and again chromatographed over a column of 150 g. of silica gel, eluting with chloroform:methanol (2:1). The fractions containing the desired product are combined and evaporated to dryness at 40° C. under reduced pressure and the residue is dissolved in 75 ml. of water, filtered and lyophilized. The product still contains 0.1 percent of 1-hydroxybenztriazole and is again put over a column of Dowex 1×2 ion exchange resin (chloride form) in water solution and the eluate is lyophilized to give 6.95 g. of N$^\alpha$-benzyloxycarbonyl-L-arginyl-L-prolyl-glycinamide hydrochloride; $[\alpha]_D^{23}$ −61.5° (c 1.02, 1 percent acetic acid in water); ultraviolet in methanol plus KOH $\lambda_{max}$ 257 $E_1^1$ 4.1. The product is obtained crystalline from methanol (25 ml.), ethyl acetate (added until just cloudy), chloroform (5 ml.), dry diethyl ether (added until just cloudy) and cooling overnight. Recrystallization from 17 ml. of methanol and 40 ml. of ethyl acetate yield 5.9 g.; melts to a foam at 140° to 145° C.; $[\alpha]_D^{23}$ −62° (c 1.02, 1 percent acetic acid in water); ultraviolet in methanol plus KOH, $\lambda_{max}$ 257.5 $E_1^1$ 4.05.

(n)

N$^\alpha$-Benzyloxycarbonyl-O-benzyl-L-seryl-L-tryptophyl-L-seryl-L-tyrosyl-D-phenylalanyl-L-leucyl-L-arginyl-L-prolyl-glycinamide hydrochloride N$^\alpha$-Benzyloxycarbonyl-L-arginyl-L-prolyl-glycinamide hydrochloride, 1.4 g., is dissolved in 60 ml. of absolute methanol, 400 mg. of 10 percent palladium-on-carbon added and the flask flushed with nitrogen. The atmosphere is replaced with hydrogen and the mixture stirred with hydrogen for forty-five minutes. Completion of the reaction is demonstrated by thin layer chromatography. The flask is flushed with nitrogen and the catalyst removed by filtration. The filtrate is evaporated to 900 mg. of a glass and is used without further purification.

N$^\alpha$-Benzyloxycarbonyl-O-benzyl-L-seryl-L-tryptophyl-L-seryl-L-tyrosyl-D-phenylalanyl-L-leucyl hydrazide, 2.12 g., is dissolved in 80 ml. of dimethylformamide and is cooled to −20° C. with stirring. The solution is treated with 4.93 ml. (6 equivalents) of 2.42N hydrogen chloride in tetrahydrofuran and then with 0.42 ml. of isopentylnitrite. The mixture is stirred at −20° C. for 30 minutes, cooled to −25° C. and treated with 1.66 ml. of triethylamine (6 equivalents). The L-arginyl-L-prolyl-glycinamide hydrochloride obtained above is added and the reaction stirred at −20° C. for 30 minutes; at 0°-5° C. (ice bath) for 3 hours and is then let stand overnight at 0°-5° C. in a refrigerator. The mixture is filtered and the solution evaporated. The residue is triturated with tetrahydrofuran, decanted and the residue taken into 20 ml. of methanol and added dropwise to 250 ml. of ethyl acetate with stirring. The mixture is let stand overnight in the refrigerator and is filtered and dried under reduced pressure; 1.45 g. The product is purified by chromatography on silica gel, eluting with chloroform-methanol (60:45). The fractions 6 through 10 are combined on the basis of thin layer chromatography and evaporated. The residue is taken into methanol and water, adjusted to pH 4 with hydrochloric acid and the product obtained by lyophilization; 720 mg. of N$^\alpha$-benzyloxycarbonyl-O-benzyl-L-seryl-tryptophyl-L-seryl-L-tyrosyl-D-phenylalanyl-L-leucyl-L-arginyl-L-prolyl-glycinamide hydrochloride; $[\alpha]_D^{23}$ −23.4° (c 1.0, DMF); ultraviolet in methanol $\lambda_{max}$ 289.5 $E_1^1$ 39.1; $\lambda_{max}$ 280 $E_1^1$ 51.0.

EXAMPLE 2

N$^\alpha$-BENZYLOXYCARBONYL-L-GLUTAMINYL-L-TRYPTOPHYL-L-SERYL-L-TYROSYL-D-PHENYLALANYL-L-LEUCYL-L-ARGINYL-L-PROLYLGLYCINAMIDE (a) L-Seryl-L-tyrosine methyl ester hydrochloride Methanol (70 ml.) containing 6.67 ml. of 3N hydrogen chloride in tetrahydrofuran is added to a mixture of 8.328 g. of N$^\alpha$-benzyloxycarbonyl-L-seryl-L-tyrosine methyl ester [cf. Fischer and Whetstone, J. Am. Chem. Soc., 76, 5076 (1954)] and 500 mg. of 20% palladium-on-carbon and the resulting mixture stirred under hydrogen at one inch water pressure for three hours. The mixture is filtered to remove the catalyst and the filtrate is evaporated to dryness under reduced pressure to give a residue of L-seryl-L-tyrosine methyl ester hydrochloride which is suitable for use without further purification.

(b)

N$^\alpha$-Benzyloxycarbonyl-L-tryptophyl-L-seryl-L-tyrosine methyl ester

L-Seryl-L-tyrosine methyl ester hydrochloride (taken directly from part a) and 11.7 g. of N$^\alpha$-benzyloxycarbonyl-L-tryptophan pentachlorophenyl ester [cf. Kovacs et al. J. Org. Chem. 32, 3696 (1967)] are dissolved in 60 ml. of dimethylformamide, cooled to −10° C. with stirring and treated with 28 ml. of triethylamine. The reaction is stirred 1½ hours at −10° C. and allowed to warm to room temperature with stirring overnight. The mixture is filtered and the filtrate evaporated at 50° C. and reduced pressure. The residue is twice dissolved in methanol and the solvent removed under reduced pressure. The residue is then again taken into 30 ml. of methanol and precipitated by addition of 300 ml. of ether and 100 ml. of petroleum ether. The precipitated oil is obtained by decantation and stirred with 30 ml. of hot ethyl acetate. The product is obtained by cooling and precipitating by addition of ether and petroleum ether. It is further purified by repeating the precipitation from methanol with petroleum ether. The supernatant is decanted and the oil dried at 50° C. and under reduced pressure. The product thus obtained is a tan foam which can be crystallized from methanol, ether and petroleum ether by seeding; m.p. 149°-152° C.; $[\alpha]_D^{23}$ −1.8° (c 1.00, methanol); ultraviolet in methanol, $\lambda_{max}$ 289.5 $E_1^1$ 92, $\lambda_{max}$ 280 $E_1^1$ 122.

(c) L-Tryptophyl-L-seryl-L-tyrosine methyl ester hydrochloride

Methanol (75 ml.) containing 1.7 ml. of 3N hydrogen chloride in tetrahydrofuran is added to a mixture of 3.1 g. of N$^\alpha$-benzyloxycarbonyl-L-tryptophyl-L-seryl-L-tyrosine methyl ester and 200 mg. of 20% palladium-on-carbon and the reaction is stirred under an atmosphere of hydrogen for two and a half hours. The mixture is filtered to remove the catalyst and the filtrate is evaporated under reduced pressure to give a residue of L-tryptophyl-L-seryl-L-tyrosine methyl ester hydrochloride which is suitable for use without further purification.

(d) N$^\alpha$-Benzyloxycarbonyl-L-glutaminyl-L-tryptophyl-L-seryl-L-tyrosine methyl ester A mixture of the product from (c) above, 1.4 g. of N$^\alpha$-benzyloxycarbonyl-L-glutamine, 670 mg. of 1-hydroxybenztriazole and 50 ml. of dimethylformamide is stirred and cooled to −10° C., and 0.7 ml. of triethylamine is added. After 15 minutes, it is treated with 1.2 g. of dicyclohexylcarbodiimide and stirred a few hours at −10° C., then at room temperature for two days and finally let stand an additional three days. The solution is filtered and the filtrate evaporated at 50° C. under reduced pressure. The residue is precipitated from methanol with water and then crystallized from methanol three times; m.p. 245°–248° C.; $[\alpha]_D^{25}$ −4.4° (c 1, DMF); ultraviolet in methanol, $\lambda_{max}$ 290 $E_1^1$ 75.7; $\lambda_{max}$ 280 $E_1^1$ 100.

(e) N$^\alpha$-Benzyloxycarbonyl-L-glutaminyl-L-tryptophyl-L-seryl-L-tyrosyl hydrazide A solution of 1.6 g. of N$^\alpha$-benzyloxycarbonyl-L-glutaminyl-L-tryptophyl-L-seryl-L-tyrosine methyl ester in 17 ml. of dimethylformamide is cooled to 30° C. and treated with 3 ml. of hydrazine hydrate. The reaction is maintained at 30° for a half hour. The solution is filtered and the filtrate is warmed to 50°–60° C. for 10 minutes and then let stand overnight at 25°. The solid is filtered off and washed with methanol. The wet solid is boiled in 25 ml. of methanol, let cool, and filtered, washing with methanol and ether. The product is dried at 50° C. under reduced pressure; m.p. 260°–270° C.; $[\alpha]_D^{25}$ −10.0° (c 1, DMF); ultraviolet in methanol $\lambda_{max}$ 289.7 $E_1^1$ 77.2; $\lambda_{max}$ 279 $E_1^1$ 102.

(f) L-Arginyl-L-prolyl-glycinamide hydrochloride

A solution of 21.2 g. of N$^\alpha$-benzyloxycarbonyl-L-arginyl-L-prolyl-glycinamide hydrochloride (Example 1, part m) in 200 ml. of methanol with 1.0 g. of 20% palladium-on-carbon is stirred under hydrogen gas for four hours and allowed to stand overnight. The solution is filtered and the filtrate evaporated at 40° C. under reduced pressure to a white foam which is suitable for use without further purification.

(g) N$^\alpha$-Benzyloxycarbonyl-L-leucyl-L-arginyl-L-prolyl-glycinamide hydrochloride A solution of L-arginyl-L-prolyl-glycinamide hydrochloride (from de-protection of 21.2 g. of N$^\alpha$-benzyloxycarbonyl-L-arginyl-L-prolyl-glycinamide hydrochloride), 17 g. of N$^\alpha$-benzyloxycarbonyl-L-leucine p-nitrophenyl ester and 85 ml. of dimethylformamide is allowed to stand at 25° C. for 48 hours, warmed to 50° C. for 10 minutes and let stand for six hours at 25° C. The solution is poured slowly into 800 ml. of stirred dry diethyl ether. The sticky solid is separated by decanting, dissolved in 50 ml. of methanol with warming and the solution poured into 500 ml. of stirred ether. The solid is separated and dried at 40° C. under reduced pressure. It is dissolved in 50 ml. of methanol and 450 ml. of chloroform and chromatographed over a column of 170 g. of silica gel (prepared in 10% methanol in chloroform) and eluted with 10 to 20% methanol in chloroform. The desired fractions, as shown by thin layer chromatography, are combined and evaporated to dryness at 40° C. under reduced pressure and the residue is dissolved in 50 ml. of methanol and 25 ml. of ethyl acetate and the solution is dropped slowly into 350 ml. of stirred dry ether. The solid is separated and dried at 40° C. under reduced pressure to give N$^\alpha$-benzyloxycarbonyl-L-leucyl-L-arginyl-L-prolyl-glycinamide hydrochloride; 11.6 g.; $[\alpha]_D^{23}$ −51.6° (c 1.0, methanol); ultraviolet in methanol $\lambda_{max}$ 257 $E_1^1$ 3.24.

(h) L-Leucyl-L-arginyl-L-prolyl-glycinamide hydrochloride

A solution of 6.43 g. of N$^\alpha$-benzyloxycarbonyl-L-leucyl-L-arginyl-L-prolyl-glycinamide hydrochloride in 200 ml. of methanol with 250 mg. of 20% palladium-on-carbon is stirred under hydrogen gas for three hours, the catalyst removed by filtration, and the filtrate evaporated to dryness at 45° C. under reduced pressure. The dried residue is a foam which is suitable for use without further purification.

(i) N$^\alpha$-Benzyloxycarbonyl-D-phenylalanyl-L-leucyl-L-arginyl-L-prolyl-glycinamide hydrochloride The L-leucyl-L-arginyl-L-prolyl-glycinamide hydrochloride obtained from de-protection of 6.43 g. of N$^\alpha$-benzyloxy-carbonyl-L-leucyl-L-arginyl-L-prolyl-glycinamide hydrochloride, 4.3 g. of N$^\alpha$-benzyloxycarbonyl-D-phenylalanine p-nitrophenyl ester (prepared as for the L-isomer, J. Org. Chem. 27, 3409 (1962)) and 30 ml. of dimethylformamide is stirred until solution is complete. The solution is allowed to stand at 25° C. for 24 hours, filtered from a small amount of fine solid and again allowed to stand at 25° C. for 24 hours. The solution is evaporated to dryness at 40° C. under reduced pressure. The residue is dissolved in methanol (40 ml.) and ethyl acetate (30 ml.) and dropped into 300 ml. of stirred dry diethyl ether. The granular solid which precipitates is separated by decanting and the precipitation is repeated. The solid is separated and dried at 45° C. under reduced pressure to give 6.5 g. of product suitable for use but showing by ultraviolet absorption 0.37% of p-nitrophenol; $[\alpha]_D^{23}$ −54.6° (c 1.0, methanol); ultraviolet in methanol $\lambda_{max}$ 257 $E_1^1$ 5.8.

(j) D-Phenylalanyl-L-leucyl-L-arginyl-L-prolyl-glycinamide hydrochloride

A solution of 3.9 g. of N$^\alpha$-benzyloxycarbonyl-D-phenylalanyl-L-leucyl-L-arginyl-L-prolyl-glycinamide hydrochloride in 100 ml. of methanol with 500 mg. of 20% palladium-on-carbon is stirred under hydrogen gas at slightly above atmospheric pressure for four hours. The solution is filtered and the filtrate is evaporated to dryness at 40° C. under reduced pressure to give a white foam suitable for use without further purification.

(k) N$^\alpha$-Benzyloxycarbonyl-L-glutaminyl-L-tryptophyl-L-seryl-L-tyrosyl-D-phenylalanyl-L-leucyl-L-arginyl-L-prolyl-glycinamide A solution of 3.68 g. of N$^\alpha$-benzyloxycarbonyl-L-glutaminyl-L-tryptophyl-L-seryl-L-tyrosyl hydrazide in 90 ml. of dimethylformamide is cooled to 0° C. and treated with 8.8 ml. of 3.4N hydrogen chloride in tetrahydrofuran with stirring. At 10° C., the hydrazide is completely dissolved in one half hour and the solution is cooled to −20° C. and 0.84 ml. of isopentylnitrite is added. The reaction is stirred at −40° to 15° for 3 hours and 4.2 ml. of triethylamine is added, followed by a solution of D-phenylalanyl-L-leucyl-L-arginyl-L-prolyl-glycinamide hydrochloride (obtained by de-protection of 3.9 g. of $N^\alpha$-benzyloxycarbonyl-D-phenyl-alanyl-L-leucyl-L-arginyl-L-prolyl-glycinamide hydrochloride) in 30 ml. of dimethylformamide. The reaction is stirred at $-20°$ C. for 2 hours, allowed to warm to 20° C. in 1 hour and stirred for 20 hours. The solution is filtered and the filtrate is evaporated at 45° C. under reduced pressure. The residue is dissolved in 50 ml. of methanol and the solution is added dropwise to 100 ml. of ethyl acetate while stirring. The tan solid which separates is filtered off, dissolved in 30 ml. of warm methanol, and 20 ml. of ethyl acetate and 50 ml. of chloroform added slowly to the warm solution. The solution is cooled in ice for one hour and the solid is filtered off, washed with ethyl acetate and dried at 40° C. under reduced pressure; 6.3 g. A part of this product (600 mg.) is stirred with 10 ml. of warm methanol and the solution is cooled and filtered. The solid which separates is washed with 5 ml. of methanol. The filtrate (15 ml.) is diluted with 15 ml. of chloroform and chromatographed over a column (1.2×12 cm) of 6 g. of silica gel (prepared in chloroform), eluting the column with increasing concentrations of methanol (5 to 20%) in chloroform. The fractions containing the desired product as shown by thin layer chromatography are combined and evaporated to dryness at 40° under reduced pressure and the residue is dissolved in 5 ml. of methanol and allowed to stand and slowly evaporate. The solid which separates is filtered off, washed with ether, and dried at 50° C. under reduced pressure to give $N^\alpha$-benzyloxycarbonyl-L-glutaminyl-L-tryptophyl-L-seryl-L-tyrosyl-D-phenylalanyl-L-leucyl-L-arginyl-L-prolyl-glycinamide hydrochloride; 120 m.g.; $[\alpha]_D^{23}$ $-60.5°$ (c 1.0, methanol); ultraviolet in methanol $\lambda_{max}$ 289.5 $E_1^1$ 42.6; $\lambda_{max}$ 280 $E_1^1$ 55.8.

The remainder of the product (5.7 g.) is stirred in 25 ml. of methanol at 50° C., allowed to cool and stand at 20° C., and the solid filtered off and washed with a little cold methanol. This process is repeated with 30 ml. of methanol and the solid separated by filtration and washed with cold methanol and dry ether and dried at 35° C. under reduced pressure; 3.7 g. The solid is dissolved in 300 ml. of hot methanol with stirring, the solution is filtered and the filtrate is put over a column (2.4×25 cm) of 50 g. of Dowex 1×2 ion exchange resin (acetate form) and the product eluted with methanol. Fractions containing the desired product as shown by thin layer chromatography are combined and filtered. The filtrate is concentrated to 75 ml. by a stream of warm, filtered air and the solution is allowed to stand overnight. Solvent is pipetted from the gel which precipitates and the gel is washed with methanol (5 ml.) twice, pipetting off the solvent. The gel is stirred with dry diethyl ether (150 ml.) for one hour, filtered, and the solid washed with ether and dried at 50° C. under reduced pressure to give $N^\alpha$-benzyloxycarbonyl-L-glutaminyl-L-tryptophyl-L-seryl-Ltyrosyl-D-phenylalanyl-L-leucyl-L-arginyl-L-prolyl-glycinamide acetic acid salt; 3.24 g.; $[\alpha]_D^{23}$ $-63°$ (c 1.007, methanol); ultraviolet in methanol $\lambda_{max}$ 289.5 $E_1^1$ 41.9; $\lambda_{max}$ 280 $E_1^1$ 54.5.

EXAMPLE 3

$N^\alpha$-t-BUTOXYCARBONYL-O-BENZYL-L-SERYL-L-TRYPTOPHYL-L-SERYL-L-TYROSYL-D-TRYPTOPHYL-L-LEUCYL-L-ARGINYL-L-PROLYLGLYCINAMIDE (a)

$N^\alpha$-t-Butoxycarbonyl-O-benzyl-L-seryl-L-tryptophyl-L-seryl-L-tyrosyl hydrazide A solution of 4.2 g. of $N^\alpha$-benzyloxycarbonyl-L-tryptophyl-L-seryl-L-tyrosine methyl ester (Example 2, part b) in 100 ml. of methanol with 300 mg. of 20% palladium-on-carbon is stirred under hydrogen gas for 2.5 hours and the solution is filtered from the catalyst. $N^\alpha$-t-Butoxycarbonyl-O-benzyl-L-serine 2.1 g., is added to the filtrate and the solution is evaporated to dryness at 50° C. uner reduced pressure. The residue is dissolved in 50 ml. of dimethylformamide with addition of 950 mg. of 1-hydroxybenztriazole. After solution is complete, the reaction is cooled to $-10°$ C. and treated with 1.6 g. of N,N'-dicyclohexylcarbodiimide with stirring. The reaction is stirred at $-10°$ C. for 1.5 hours, allowed to warm to 20° C. and stirred for 20 hours. The solution is filtered and the filtrate is evaporated to dryness under reduced pressure. The residue is dissolved in 250 ml. of ethyl acetate and the solution is washed with 100 ml. of 7% sodium bicarbonate solution in three portions, with 20 ml. of water, with 20 ml. of dilute hydrochloric acid, with saturated salt solution and is dried with magnesium sulfate and evaporated to dryness at 40° C. under reduced pressure. The residue is dissolved in methanol and again evaporated to dryness. The residue is dissolved in 50 ml. of hot methanol, cooled, the solution filtered and 3.5 ml. of hydrazine hydrate added with good mixing. After twenty hours, the solution is cooled in ice and the solid separated and washed with a little cold methanol. The solid is stirred with warm methanol and, after standing, is chilled in ice, filtered and the solid is washed with cold methanol, then with dry ether, and dried to give 3.5 g. of $N^\alpha$-t-butoxycarbonyl-O-benzyl-L-seryl-L-tryptophyl-L-tyrosyl hydrazide; m.p. 195°–200° C.; $[\alpha]_D^{23}$ $-13.7°$ (c 1.0, methanol); ultraviolet in methanol $\lambda_{max}$ 289.5 $E_1^1$ 73.5; $\lambda_{max}$ 280 $E_1^1$ 96.5.

(b)

$N^\alpha$-t-Butoxycarbonyl-D-tryptophyl-L-leucyl-L-arginyl-L-prolyl-glycinamide hydrochloride L-Leucyl-L-arginyl-L-prolyl-glycinamide hydrochloride (Example 2, part h) from 5.13 g. of $N^\alpha$-benzyloxycarbonyl-L-leucyl-L-arginyl-L-prolyl-glycinamide hydrochloride, 2.43 g. of $N^\alpha$-t-butoxycarbonyl-D-tryptophan (prepared as for the L-isomer, J. Chem. Soc., 1964, 6130), 100 ml. of dimethylformamide and 1.1 g. of 1-hydroxybenztriazole are stirred together until solution is complete and the solution is then cooled to $-10°$ C. and 1.9 g. of N,N'-dicyclohexylcarbodiimide added. The solution is allowed to warm slowly to 25° C. and is stirred for 48 hours at 25° C. The solution is filtered and the filtrate evaporated to dryness at 50° C. under reduced pressure. The residue is dissolved in 35 ml. of warm methanol, 25 ml. of ethyl acetate is added and the solution filtered. The filtrate is dropped into 300 ml. of stirred dry ether to precipitate a solid. The solid is separated, dissolved in 25 ml. of methanol and 15 ml. of ethyl acetate and again precipitated with dry ether. The solid is washed with ether and dried at 40° under reduced pressure to give 6.2 g. of $N^\alpha$-t-butoxycarbonyl- D-tryptophyl-L-leucyl-L-arginyl-L-prolyl-glycinamide hydrochloride; $[\alpha]_D^{23}$ −54.2° (c 1.035, methanol); ultraviolet in methanol $\lambda_{max}$ 290 $E_1^1$ 63; $\lambda_{max}$ 281 $E_1^1$ 71; $\lambda_{max}$ 274 $E_1^1$ 65.6.

(c)

D-Tryptophyl-L-leucyl-L-arginyl-L-prolyl-glycinamide dihydrochloride

A solution of 1.69 g. of $N^\alpha$-t-butoxycarbonyl-D-tryptophyl-L-leucyl-L-arginyl-L-prolyl-glycinamide hydrochloride in 20 ml. of methanol and 10 ml. of 3N hydrogen chloride in 10 ml. of tetrahydrofuran is allowed to stand for 1 hour and then evaporated to dryness at 30° C. under reduced pressure. The residue is twice dissolved in 20 ml. of methanol and the solvent evaporated. It is then dried at 45° C. under reduced pressure. The product is used without further purification.

(d)

$N^\alpha$-t-Butoxycarbonyl-O-benzyl-L-seryl-L-tryptophyl-L-seryl-L-tyrosyl-D-tryptophyl-L-leucyl-L-arginyl-L-prolyl-glycinamide 3N Hydrogen chloride (2.66 ml.) in a tetrahydrofuran is added to a solution of 1.51 g. of $N^\alpha$-t-butoxycarbonyl-O-benzyl-L-seryl-L-tryptophyl-L-seryl-L-tyrosyl hydrazide in 30 ml. of dimethylformamide at −35° C. followed by the addition of 0.35 ml. of isopentylnitrite. The solution is stirred at −16° C. to −23° C. for 50 minutes, cooled to −40° C. and 1.4 ml. of triethylamine is added, followed by a solution of D-tryptophyl-L-leucyl-L-arginyl-L-prolyl-glycinamide dihydrochloride in 20 ml. of dimethylformamide. After stirring at −15° C. to −20° C. for 1.5 hours, 0.28 ml. of triethylamine is added and the solution is stirred at −10° C to 0° C. for ½ hour, at 0° to 20° C. for 1 hour and at 20° C. for 20 hours. The solution is filtered and the filtrate evaporated to dryness at 40° C. under reduced pressure. The residue is dissolved in 25 ml. of warm methanol, 20 ml. of ethyl acetate added and the solution dropped into 300 ml. of dry diethyl ether with stirring. The tan solid is filtered off and dried; 3.25 g. The solid is dissolved in 20 ml. of methanol and 20 ml. of ethyl acetate, 0.5 ml. of 3N hydrogen chloride in tetrahydrofuran added and the solution dropped into 250 ml. of dry stirred ether. The tan solid is separated by filtration, dissolved in 20 ml. of methanol and 50 ml. of chloroform and chromatographed over a column (1.4×35 cm) of 30 g. of silica gel (prepared in chloroform) eluting with chloroform and a mixture of 5 to 15% methanol in chloroform. The desired fractions as shown by thin layer chromatography are combined, concentrated, and the product precipitated by the addition of ethyl acetate. The solid is separated, washed with ethyl acetate and dried at 50° C. under reduced pressure to give $N^\alpha$-t-butoxycarbonyl-O-benzyl-L-seryl-L-tryptophyl-L-seryl-L-tyrosyl-D-tryptophyl-L-leucyl-L-arginyl-L-prolyl-glycinamide hydrochloride; $[\alpha]_D^{23}$ −41.8° (c 1.0, methanol); ultraviolet in methanol $\lambda_{max}$ 289.5 $E_1^1$ 71.8; $\lambda_{max}$ 280 $E_1^1$ 86.8.

EXAMPLE 4

$N^\alpha$-BENZYLOXYCARBONYL-L-GLUTAMINYL-L-TRYPTOPHYL-L-SERYL-L-TYROSYL-D-TRYPTOPHYL-L-LEUCYL-L-ARGINYL-L-PROLYL-GLYCINAMIDE A solution of 1.46 g. of $N^\alpha$-benzyloxycarbonyl-L-glutaminyl-L-tryptophyl-L-seryl-L-tyrosyl hydrazide (Example 2, part (e) in 35 ml. of dimethylformamide is cooled to 10° C. with stirring and treated with 4 ml. of 3N hydrogen chloride in tetrahydrofuran. When the hydrazide is completely dissolved, the solution is cooled to −20° C. and 0.36 ml. of isopentylnitrite is added. The reaction is stirred at −20° C. for 3 hours, cooled to −30° C. and treated with 1.96 ml. of triethylamine. D-Tryptophyl-L-leucyl-L-arginyl-L-prolyl-glycinamide dihydrochloride, prepared from 1.69 g. of $N^\alpha$-t-butoxycarbonyl-D-tryptophyl-L-leucyl-L-arginyl-L-prolyl-glycinamide hydrochloride (this protected material is prepared according to Example 3, part (b), is dissolved in 20 ml. of dimethylformamide and added to the reaction. The solution is stirred at −30° C. to 13° C. for 3 hours, allowed to warm to 20° C. and stirred for 20 hours. Triethylamine, 0.6 ml., is added and stirring continued at 20° C. for 24 hours. Hydrogen chloride, 1.4 ml. of 3N in tetrahydrofuran, is added and the reaction stirred for three hours. The solution is filtered and the filtrate evaporated to dryness at 40° C. under reduced pressure. The residue is stirred with methanol and the solvent again evaporated. The residue is dissolved in 25 ml. of methanol and treated slowly with ethyl acetate until close to the point of precipitation. The solution is allowed to stand. The insoluble gel-like solid which separates is obtained by filtration and is washed with a little methanol-ethyl acetate mixture. The solid is dissolved in a small amount of methanol and precipitated by dropping the solution into an excess of stirred dry ether (150 ml.). The gel is separated by filtering through a dense filter paper, washing with dry ether and drying at 50° C. under reduced pressure; $N^\alpha$-benzyloxycarbonyl-L-glutaminyl-L-tryptophyl-L-seryl-L-tyrosyl-D-tryptophyl-L-leucyl-L-arginyl-L-prolyl-glycinamide hydrochloride; 170 mg.; $[\alpha]_D^{23}$ −59° (c. 1.0, methanol); ultraviolet in methanol $\lambda_{max}$ 290 $E_1^1$ 73; $\lambda_{max}$ 281 $E_1^1$ 88.

Additional product may be obtained from the filtrate of the initial gel-like solid by precipitation with excess dry ether. It is purified by fractional precipitation of a methanol solution with increasing additions of ethyl acetate. The fractions are inspected by thin layer chromatography, combined and chromatographed over a silica gel column. Thus 850 mg. of solid dissolved in 30 ml. of methanol and 50 ml. of chloroform is chromatographed over a column (1.8×23 cm) of 30 g. of silica gel, eluting with 10 to 20% methanol in chloroform. The fractions are selected by thin layer chromatography, combined, concentrated to a small volume and allowed to stand at 20° C. The solid which precipitates is separated, washed with a small amount of methanol, then with ether, and is dried at 50° C. under reduced pressure; 160 mg.; $[\alpha]_D^{23}$ −52.8° (c 1.0, methanol); ultraviolet in methanol $\lambda_{max}$ 289.5 $E_1^1$ 75.2; $\lambda_{max}$ 280 $E_1^1$ 91.1.

EXAMPLE 5

$N^\alpha$-BENZYLOXYCARBONYL-O-BENZYL-L-TYROSYL-L-TRYPTOPHYL-L-SERYL-L-TYROSYL-D-LEUCYL-L-LEUCYL-L-ARGINYL-L-PROLYL-GLYCINAMIDE (a) $N^\alpha$-Benzyloxycarbonyl-D-leucyl-L-leucine methyl ester A solution of 2.65 g. of $N^\alpha$-benzyloxycarbonyl-D-leucine [This material is prepared by the same procedure as used by Grassman and Wunsch, Ber. 91, 462 (1968) for the DL-leucine and for the L-leucine see Losse and Demuth, Ber. 94, 1762 (1961). The material is an oil as described for the $N^\alpha$-benzyloxycarbonyl-L-leucine enantiomer. See also Farthing, J. Chem. Soc. 1950, 3213 and Bergmann, J. Biol. Chem., 115, 593 (1936).] in 50 ml. of dimethylformamide is treated with 1.98 g. of L-leucine methyl ester hydrochloride and cooled in an ice bath. The solution is treated with 1.4 ml. of triethylamine, then with 1.5 g. of 1-hydroxybenztriazole, and finally with 2.26 g. of dicyclohexylcarbodiimide. The reaction is stirred overnight with initial ice bath cooling and gradual warming to room temperature, and then an additional 24 hours at room temperature. The mixture is filtered and the filtrate evaporated. The residue is dissolved in ethyl acetate and the solution washed with 1N hydrochloric acid, saturated sodium chloride solution, 5% sodium bicarbonate solution and again with saturated sodium chloride solution. The ethyl acetate solution is separated and dried over magnesium sulfate, filtered and evaporated. The residue crystallizes and is recrystallized from isopropyl ether; $[\alpha]_D^{23} -5.3°$ (c 2.06, methanol), m.p. 80°-82° C.

(b)

$N^\alpha$-Benzyloxycarbonyl-L-tryptophyl-L-seryl-L-tyrosyl-D-leucyl-L-leucine methyl ester $N^\alpha$-Benzyloxycarbonyl-D-leucyl-L-leucine methyl ester, 1.95 g., is dissolved in 50 ml. of absolute methanol, treated with 2.33 ml. of 2.145N hydrogen chloride in methanol and 250 mg. of 10% palladium-on-carbon and reduced as in earlier examples to give 1.4 g. of D-leucyl-L-leucine methyl ester hydrochloride.

$N^\alpha$-Benzyloxycarbonyl-L-tryptophyl-L-seryl-L-tyrosyl hydrazide, 2.4 g., is dissolved in 80 ml. of dimethylformamide and cooled to −20° C. The solution is treated with 9.87 ml. of 2.42N hydrogen chloride in tetrahydrofuran and then with 0.756 ml. of isopentylnitrite. The reaction is stirred at −20° C. for 30 minutes, cooled to −25° C. and treated with 3.9 ml. of triethylamine. The above D-leucyl-L-leucine methyl ester hydrochloride, 1.3 g., is added and the reaction stirred at −20° C. for 30 minutes, at −20° to −5° C. for 30 minutes and at 0° C. for 3 hours. The reaction is then stored overnight at 0° C. The mixture is filtered and the filtrate evaporated under reduced pressure. The residue is suspended in 600 ml. of ethyl acetate and 20 ml. of water and is treated with 30 ml. of 0.5N hydrochloric acid. The ethyl acetate is separated and washed with saturated salt solution, sodium bicarbonate solution, and again with saturated salt solution. The ethyl acetate is filtered and evaporated to about 50 ml. volume. This is stored at 0° C. for one day, treated with ether to aid precipitation, filtered, and the solid dried under reduced pressure; 2.35 g. of $N^\alpha$-benzyloxycarbonyl-L-tryptophyl-L-seryl-L-tyrosyl-D-leucyl-L-leucine methyl ester.

(c)

$N^\alpha$-Benzyloxycarbonyl-O-benzyl-L-tyrosyl-L-tryptophyl-L-seryl-L-tyrosyl-D-leucyl-L-leucine methyl ester $N^\alpha$-Benzyloxycarbonyl-L-tryptophyl-L-seryl-L-tyrosyl-D-leucyl-L-leucine methyl ester, 2.3 g., is dissolved in 70 ml. of absolute methanol and treated with 500 mg. of 20% palladium-on-carbon. The flask is flushed with nitrogen and then with hydrogen and the hydrogenation run for forty-five minutes. Reaction completion is checked by thin layer chromatography. The flask is flushed with nitrogen, the catalyst removed by filtration and the filtrate evaporated. The product is dried under reduced pressure; 2.0 g.

The above product, 2.0 g. of L-tryptophyl-L-seryl-L-tyrosyl-D-leucyl-L-leucine methyl ester, is dissolved in 70 ml. of dimethylformamide and cooled in an ice bath. $N^\alpha$-Benzyloxycarbonyl-O-benzyl-L-tyrosine, 970 mg., 355 mg. of 1-hydroxybenztriazole and 545 mg. of dicyclohexylcarbodiimide are added. The reaction is stirred at ice bath temperature for several hours, then to room temperature and finally at room temperature for twenty-four hours. The mixture is filtered and the filtrate evaporated under reduced pressure. The residue is dissolved in 400 ml. of ethyl acetate, 20 ml. of water and 20 ml. of 0.5N hydrochloric acid. The ethyl acetate is separated, washed with saturated salt solution, with 0.5N sodium bicarbonate solution, again with saturated salt solution and is evaporated to a solid residue; 2.81 g.

(d)

$N^\alpha$-Benzyloxycarbonyl-O-benzyl-L-tyrosyl-L-tryptophyl-L-seryl-L-tyrosyl-D-leucyl hydrazide $N^\alpha$-Benzyloxycarbonyl-O-benzyl-L-tyrosyl-L-tryptophyl-L-seryl-L-tyrosyl-D-leucyl-L-leucine methyl ester, 2.81 g., is dissolved in 20 ml. of dimethylformamide and 30 ml. of methanol. The solution is treated with 3 ml. of hydrazine hydrate and let stand at room temperature for three days. The solution is filtered and the filtrate evaporated to remove methanol. The remaining dimethylformamide solution is diluted with 200 ml. of isopropanol and let stand at room temperature for 1 hour and overnight at 0° C. The mixture is filtered to separate the precipitate. The solid is triturated with ether for 2 hours, then separated and dried under reduced pressure; 1.8 g. The filtrate gives a small additional amount on evaporation and treatment with isopropanol. The product has $[\alpha]_D^{23} -13°$ (c 1.0, DMF); ultraviolet in methanol $\lambda_{max} 289$ $E_1^1 54.4$; $\lambda_{max} 282.5$ $E_1^1 80.4$; $\lambda_{max} 278$ $E_1^1 81$.

(e)

$N^\alpha$-Benzyloxycarbonyl-O-benzyl-L-tyrosyl-L-tryptophyl-L-seryl-L-tyrosyl-D-leucyl-L-leucyl-L-arginyl-L-prolyl-glycinamide $N^\alpha$-Benzyloxycarbonyl-L-arginyl-L-prolyl-glycinamide hydrochloride, (Example 1, part m) 1.2 g., is dissolved in 60 ml. of absolute methanol, treated with 380 mg. of 10% palladium-on-carbon and the flask flushed with nitrogen, then with hydrogen and the reduction carried out for 40 minutes. Completion of the reaction is determined by thin layer chromatography. The mixture is filtered to separate the catalyst and the filtrate is evaporated and dried under reduced pressure to yield L-arginyl-L-prolyl-glycinamide hydrochloride.

$N^\alpha$-Benzyloxycarbonyl-O-benzyl-L-tyrosyl-L-tryptophyl-L-seryl-L-tyrosyl-D-leucyl-L-leucyl hydrazide, 1.9 g., is dissolved in 80 ml. of dimethylformamide and cooled to −20° C. The solution is treated with 3.84 ml. of 2.74N hydrogen chloride in tetrahydrofuran and then with 0.37 ml. (10% excess) of isopentylnitrite. The mixture is stirred at −20° C. for 30 minutes, cooled to −25° C., treated with 1.46 ml. of distilled triethylamine and then with the above L-arginyl-L-prolyl-glycinamide hydrochloride, 700 mg. The reaction is stirred at −20° C. for 30 minutes, at −20° to −10° C. for 15 minutes and at ice-bath temperature for three hours. It is then stored at 0° to 5° C. overnight. The mixture is filtered and the filtrate evaporated under reduced pressure. The residue is triturated with tetrahydrofuran for three hours in the cold, decanted and the residue dissolved in 20 ml. of methanol and dropped into 250 ml. of ethyl acetate. The mixture is let stand for three hours and is filtered and the solid dried under reduced pressure.

The product is purified by chromatography on silica gel, eluting with chloroform-methanol (60:45). Fractions 7 through 10 are combined on the basis of thin layer chromatography and evaporated. The residue is dissolved in 200 ml. of water, adjusted to pH 4 with dilute hydrochloric acid and lyophilized to yield 860 mg. of $N^\alpha$-benzyloxycarbonyl-O-benzyl-L-tyrosyl-L-tryptophyl-L-seryl-L-tryrosyl-D-leucyl-L-arginyl-L-prolyl-glycinamide hydrochloride; $[\alpha]_D^{23}$ −33.2° (c 1.0, DMF); ultraviolet in methanol $\lambda_{max}$ 289.5 $E_1^1$ 40.4; $\lambda_{max}$ 282.5 $E_1^1$ 59.4; $\lambda_{max}$ 278 $E_1^1$ 60.2.

EXAMPLE 6

$N^\alpha$-BENZYLOXYCARBONYL-L-LEUCYL-L-TRYPTOPHYL-L-SERYL-L-TYROSYL-D-ASPARAGINYL-L-LEUCYL-L-ARGINYL-L-PROLYL-GLYCINAMIDE

(a) $N^\alpha$-Benzyloxycarbonyl-D-asparagine

D-Asparagine, 50 g., is dissolved in 500 ml. of water at 60° C., adding 70 g. of sodium bicarbonate and cooling to 20° C. The solution is treated with 68 g. of benzylchloroformate during one hour with stirring and is stirred for an additional two and a half hours. The solution is extracted three times with ether and the aqueous solution is acidified with cold concentrated hydrochloric acid. The white solid product is separated, washed with water and dried; 77 g.; m.p. 165°–166° C.; $[\alpha]_D^{23}$ + 7.4° (c 2.02, DMF).

(b) $N^\alpha$-Benzyloxycarbonyl-D-asparaginyl-L-leucine methyl ester $N^\alpha$-Benzyloxycarbonyl-D-asparagine, 5.325 g., and 3.814 g. of leucine methyl ester hydrochloride are dissolved in 50 ml. of dimethylformamide. The solution is cooled to 5° C. and treated slowly with 3.0 ml. of diphenylphosphorylazide in 10 ml. of dimethylformamide and 5.9 ml. of triethylamine in 10 ml. of dimethylformamide. The reaction is stirred with ice cooling for two and a half hours and at room temperature for three days. The mixture is filtered and the filtrate evaporated to dryness under reduced pressure. The residue is crystallized from ethyl acetate; 2.5 g.; m.p. 191°–193° C.; $[\alpha]_D^{25}$ −14.4° (c 1.015, DMF). A further quantity of material, 1.25 g., is obtainable from the mother liquor of the crystallization.

(c) D-Asparaginyl-L-leucine methyl ester hydrochloride $N^\alpha$-Benzyloxycarbonyl-D-asparaginyl-L-leucine methyl ester; 2.4 g., is dissolved in 70 ml. of absolute methanol and treated with 3.1 ml. of 1.97N hydrogen chloride in methanol and 250 mg. of 10% palladium-on-carbon. The flask is flushed with nitrogen and hydrogen is introduced and the flask shaken for forty minutes. Thin layer chromatography shows the reduction to be complete in 15 minutes. The catalyst is separated by filtration and the filtrate evaporated. The residue is dried at reduced pressure; 1.84 g.

(d) $N^\alpha$-Benzyloxycarbonyl-L-tryptophyl-L-seryl-L-tyrosyl-D-asparaginyl-L-leucine methyl ester $N^\alpha$-Benzyloxycarbonyl-L-tryptophyl-L-seryl-L-tyrosyl hydrazide (Example 1, part d), 2.96 g., is dissolved in 80 ml. of dimethylformamide, cooled to −20° C. and treated with 13.08 ml. of 2.788N hydrogen chloride in tetrahydrofuran (six equivalents) and then with 1.3 ml. of isopentylnitrite (90%). The reaction is stirred at −20° C. for 30 minutes, cooled to −25° C. and treated with 5.92 ml. of triethylamine (seven equivalents). D-Asparaginyl-L-leucine methyl ester hydrochloride, 1.8 g., is added and the reaction stirred at −20° C. for 30 minutes, at −20° C. to −10° C. for fifteen minutes and at 0° C. for 3 hours. The reaction is stored overnight at 0° C., filtered and the solvent evaporated under reduced pressure. The residue is dissolved in 400 ml. of ethyl acetate, 20 ml. 0f water and 20 ml. of .5N hydrochloric acid. The ethyl acetate solution is washed with saturated salt solution, 5% sodium bicarbonate solution, and again with saturated salt solution. The product separates during the washing process and is obtained by filtration. A second crop is obtained by evaporating the ethyl acetate to about 50 ml. and cooling for 2 hours; 3.81 g.

(e) L-Tryptophyl-L-seryl-L-tyrosyl-D-asparaginyl-L-leucine methyl ester $N^\alpha$-Benzyloxycarbonyl-L-tryptophyl-L-seryl-L-tyrosyl-D-asparaginyl-L-leucine methyl ester, 3.75 g. is dissolved in 200 ml. of absolute methanol, 375 mg. of 20% palladium-on-carbon added and the material reduced with hydrogen during 50 minutes. The catalyst is removed by filtration and the filtrate evaporated under reduced pressure; 1.83 g. The catalyst is extracted with 400 ml. of boiling methanol, separated by filtration and the filtrate evaporated to yield 1.22 g. of additional product.

$N^\alpha$-Benzyloxycarbonyl-L-leucyl-L-tryptophyl-L-seryl-L-tyrosyl-D-asparaginyl-L-leucine L-tyrosyl-D-asparaginyl-L-leucine methyl ester L-Tryptophyl-L-seryl-L-tyrosyl-D-asparaginyl-L-leucine methyl ester, 3.05 g., is dissolved in 100 ml. of dimethylformamide, cooled in ice and treated with 683 mg. (10% excess) of 1-hydroxybenztriazole and 1.22 g. of $N^\alpha$-benzyloxycarbonyl-L-leucine. Dicyclohexylcarbodiimide, 1.04 g. (10% excess) is added and the reaction stirred overnight, allowing the reaction to rise to room temperature as the ice melts in the cooling bath. The reaction is then stirred an additonal 24 hours at room temperature. The mixture is filtered and the solvent evaporated under reduced pressure. The residue is shaken with 650 ml. of ethyl acetate, 25 ml. of water and 20 ml. of 0.5N hydrochloric acid and filtered to separate 1.05 g. of insoluble material. The ethyl acetate solution is washed with saturated sodium chloride solution, with 5% sodium bicarbonate solution and again with saturated salt solution. The ethyl acetate solution is evaporated to one-half volume and refrigerated. The product is then separated by filtration and dried under reduced pressure; 2.3 g.; $[\alpha]_D^{23}$ −30.6° (c 1.02, DMF); ultraviolet in methanol $\lambda_{max}$ 289.5 $E_1^1$ 59.8; $\lambda_{max}$ 280 $E_1^1$ 76.8.

(g) $N^\alpha$-Benzyloxycarbonyl-L-leucyl-L-tryptophyl-L-seryl-L-tyrosyl-D-asparaginyl-L-leucyl hydrazide $N^\alpha$-Benzyloxycarbonyl-L-leucyl-L-tryptophyl-L-seryl-L-tyrosyl-D-asparaginyl-L-leucine methyl ester, 3.3 g., is dissolved in 20 ml. of dimethylformamide, 35 ml. of absolute methanol and 3.0 ml. of hydrazine hydrate and let stand overnight. Fifty ml. of isopropanol is added and the mixture again let stand overnight. The mixture is filtered, the solid suspended in 250 ml. of ether and triturated at room temperature for three hours. The product is recovered by filtration and is dried under reduced pressure; 2.78 g. of white solid, m.p. 227°–229° C.; $[\alpha]_D^{25}$ −21.5° (c 1.05, DMF), ultraviolet in methanol $\lambda_{max}$ 289.5 $E_1^1$ 51.4; $\lambda_{max}$ 280 $E_1^1$ 67.5. (h) $N^\alpha$-Benzyloxycarbonyl-L-leucyl-L-tryptophyl-L-seryl-L-tyrosyl-D-asparaginyl-L-leucyl-L-arginyl-L-prolyl-glycinamide $N^\alpha$-Benzyloxycarbonyl-L-arginyl-L-prolyl-glycinamide hydrochloride (Example 1, part m), 1.9 g., is dissolved in 75 ml. of absolute methanol and 550 mg. of 10% palladium-on-carbon added. The flask is flushed with nitrogen and then with hydrogen and the mixture stirred under hydrogen for 45 minutes. Thin layer chromatography shows the reaction to be complete in about 20 minutes. The catalyst is separated by filtration and the filtrate is evaporated and the residue dried under reduced pressure; 1.35 g.

$N^\alpha$-Benzyloxycarbonyl-L-leucyl-L-tryptophyl-L-seryl-L-tyrosyl-D-asparaginyl-L-leucyl hydrazide, 2.6 g., is dissolved in 80 ml. of dimethylformamide and the solution cooled to −20° C. and treated with 5.85 ml. of 2.722N hydrogen chloride in tetrahydrofuran followed by 0.55 ml. of isopentylnitrite. The reaction is stirred at −20° C. for thirty minutes, cooled to −25° C. and treated with 2.22 ml. of triethylamine. L-Arginyl-L-prolyl-glycinamide hydrochloride, 1.1 g., is added and the mixture stirred at −20° C. for 30 minutes, at −20° to −10° C. for 15 minutes and at about 0° C. for 3 hours. The reaction is stirred at 0° to 5° C. overnight, filtered and the solvent evaporated under reduced pressure. The residue is triturated with tetrahydrofuran, refrigerated overnight and the solid obtained by decanting. The product is dissolved in 25 ml. of methanol and dropped into 250 ml. of stirred ethyl acetate. The mixture is cooled for several hours and is filtered to separate the solid product, 3.1 g., as a hydrochloride.

The product is purified by chromatography on silica gel, eluting with chloroform-methanol (60:45). Fractions 11 through 18 are combined on the basis of thin layer chromatography and evaporated. The residue is dissolved in 100 ml. of water, adjusted to pH4 with dilute hydrochloric acid and lyophilized to yield 1.73 g. of $N^\alpha$-benzyloxycarbonyl-L-leucyl-L-tryptophyl-L-seryl-L-tyrosyl-D-asparaginyl-L-leucyl-arginyl-L-prolyl-glycinamide hydrochloride; $[\alpha]_D^{23}$ −36.4° (c 1.0, DMF), ultraviolet in methanol $\lambda_{max}$ 289.5 $E_1^1$ 42.5, $\lambda_{max}$ 280 $E_1^1$ 55.5.

EXAMPLE 7

$N^\alpha$-p-METHOXYBENZYLOXYCARBONYL-O-BENZYL-L-SERYL-L-TRYPTOPHYL-L-SERYL-L-TYROSYL-D-PHENYLALANYL-L-LEUCYL-L-ARGINYL-L-PROLYL-GLYCINAMIDE HYDROCHLORIDE (a) O-Benzyl-L-serine trifluoracetic acid salt $N^\alpha$-t-Butoxycarbonyl-O-benzyl-L-serine, 5.0 g., is treated with 20 ml. of trifluoroacetic acid at 5° C. The solution is let stand at room temperature for 15 minutes and then the excess trifluoroacetic acid removed under reduced pressure. Benzene is added followed by evaporation. This process is repeated three times to remove excess trifluoroacetic acid. Finally the product is dried under reduced pressure and used without further treatment.

(b)
$N^\alpha$-p-Methoxybenzyloxycarbonyl-O-benzyl-L-serine

O-Benzyl-L-serine trifluoroacetic acid salt, 3.09 g. in 20 ml. of water containing 0.8 g. of magnesium oxide is treated with 2.28 g. of p-methoxybenzyloxycarbonyl azide in 20 ml. of dioxane. The mixture is stirred at room temperature for four days. It is then filtered and the filtrate diluted with ethyl acetate and the solution washed with cold 0.2 N hydrochloric acid and with saturated sodium chloride solution. The ethyl acetate solution is dried and evaporated to an oil. The crude product is triturated with isopropyl ether and stored in the cold to yield crystalline material. Separation by filtration gives 1.75 g., mp. 70°–72° C. This product is recrystallized from aqueous ethanol to give 1.54 g. and is again recrystallized from ethyl acetate-hexane to yield 1.25 g. of the above named product, mp. 72°–73° C.

(c)
$N^\alpha$-p-Methoxybenzyloxycarbonyl-O-benzyl-L-seryl-L-tryptophyl-L-seryl-L-tyrosyl-D-phenylalanyl-L-leucine methyl ester L-Tryptophyl-L-seryl-L-tyrosyl-D-phenylalanyl-L-leucine methyl ester (example 1, h), 1.6 g., is dissolved in 30 ml. of dimethylformamide and treated with 0.789 g., of $N^\alpha$-p-methoxybenzyloxycarbonyl-O-benzyl-L-serine and cooled in an ice bath. 1-Hydroxybenzotriazole, 326 mg., and finally 500 mg., of dicyclohexylcarbodiimide are added and the reaction mixture stirred to room temperature overnight and for twenty-four additional hours. The reaction mixture is filtered and the solvent removed under reduced pressure. The residue is dissolved in 200 ml. of ethyl acetate and washed with 0.25 N hydrochloric acid, saturated sodium chloride solution, 5% sodium bicarbonate solution, and finally, saturated sodium chloride solution. The ethyl acetate solution is refrigerated for several days and a gelatinous precipitate separated. After triturating with ether for two hours, the above named product is separated and dried, 1.7 g.

(d)
$N^\alpha$-p-Methoxybenzyloxycarbonyl-O-benzyl-L-seryl-L-tryptophyl-L-seryl-L-tyrosyl-D-phenylalanyl-L-leucyl hydrazide $N^\alpha$-p-Methoxybenzyloxycarbonyl-O-benzyl-L-seryl-L-tryptophyl-L-seryl-L-tyrosyl-D-phenylalanyl-L-leucine methyl ester, 1.7 g., is dissolved in 15 ml. of dimethylformamide and the solution treated with 1.5 ml. of hydrazine hydrate. The reaction is let stand at room temperature overnight and added to 150 ml. of isopropanol. The precipitate is separated by filtration and dried to yield 1.58 g. of the above named product mp. 208°–210° C; $[\alpha]_D^{23}$ −13.8° (c. 1.0, DMF).

(e)
$N^\alpha$-p-Methoxybenzyloxycarbonyl-O-benzyl-L-seryl-L-tryptophyl-L-seryl-L-tyrosyl-D-phenylalanyl-L-leucyl-L-arginyl-L-prolyl-glycinamide hydrochloride $N^\alpha$-p-Methoxybenzyloxycarbonyl-O-benzyl-L-seryl-L-tryptophyl-L-seryl-L-tyrosyl-D-phenylalanyl-L-leucyl hydrazide, 1.78 g., is dissolved in 75 ml. of dimethylformamide and cooled to −20° C. The solution is treated with 3.46 ml. of 2.877 N hydrogen chloride in tetrahydrofuran. The solution is held at −20° C. with stirring, treated with 0.35 ml. of isopentyl nitrite (90%), stirred at −20° C. for 30 minutes, cooled to −25° C. and treated with 1.39 ml. of triethylamine. L-Arginyl-L-prolyl-glycinamide hydrochloride, (example 2, f), 660 mg., is added and the reaction stirred at −20° C. for 30 minutes, at −20° to −10° C. for 30 minutes, at ice-bath temperature for 3 hours and stored overnight at 0° to 5° C. The reaction mixture is then filtered and the solvent removed under reduced pressure. The residue is triturated with 200 ml. of tetrahydrofuran for three hours and cooled. The liquid is decanted and the residue dissolved in 25 ml. of methanol. The solution is added dropwise to 250 ml. of ethyl acetate with stirring, let stand in the cold overnight and the precipitated solid separated by filtration and dried under reduced pressure to give 1.89 g. of the above named product. The product is purified by chromatography over silica gel using chloroform:methanol (60:45); 1.6 g., $[\alpha]_D^{23}$ −23.4° (c 1.05, DMF).

EXAMPLE 8
N$^\alpha$-BENZYLOXYCARBONYL-L-ISOLEUCYL-L-TRYPTOPHYL-L-SERYL-L-TYROSYL-D-TRYPTOPHYL-L-LEUCYL-L-ARGINYL-L-PROLYL-GLYCINAMIDE (a) N$^\alpha$-Benzyloxycarbonyl-D-tryptophyl-L-leucine methyl ester N$^\alpha$-Benzyloxycarbonyl-D-tryptophan 6.76 g., and L-leucine methyl ester hydrochloride 3.96 g., are dissolved in 60 ml. of dimethylformamide, cooled in an ice bath and 2.77 ml., of triethylamine added dropwise. The stirred and cooled solution is then treated with 2.97 g. of 1-hydroxy-benzotriazole and 4.53 g. of dicyclohexylcarbodiimide. The reaction is stirred to room temperature in the melting ice bath and for twenty-four additional hours at room temperature. It is then filtered and the solvent evaporated under reduced pressure. The residue is dissolved in 300 ml. of ethyl acetate and the solution is washed with 0.5 N hydrochloric acid, saturated sodium chloride solution, twice with 5% sodium bicarbonate solution and finally with a saturated sodium chloride solution. The ethyl acetate solution is dried over magnesium sulfate and the solvent evaporated to leave a crystalline solid. The product is crystallized from 125 ml. of hot methanol to give 4.3 g. of N$^\alpha$-benzyloxycarbonyl-D-tryptophyl-L-leucine methyl ester, mp. 155°–156° C; $[\alpha]_D^{23}$ −21.8°, (c 2.03, methanol).

(b) D-Tryptophyl-L-leucine methyl ester hydrochloride

N$^\alpha$-Benzyloxycarbonyl-D-tryptophyl-L-leucine methyl ester, 2.75 g., and 2.65 ml. of 2.23 N hydrogen chloride are dissolved in 100 ml. of methanol followed by the addition of 300 mg. of 10% palladium-on-carbon. The reaction is stirred under a hydrogen atmosphere with hydrogen bubbling through the mixture for seventy minutes. Thin layer chromatography indicates the reaction to be complete in about 20 minutes. The mixture is filtered and the solvent evaporated. The residue is dried under reduced pressure, 2.21 g. of D-tryptophyl-L-leucine methyl ester hydrochloride, $[\alpha]_D^{23}$ −73° (c 1.02, methanol).

(c) N$^\alpha$-Benzyloxycarbonyl-L-seryl-L-tyrosyl-D-tryptophyl-L-leucine methyl ester N$^\alpha$-Benzyloxycarbonyl-L-seryl-L-tyrosyl hydrazide [cf. Hoffman, J. Am. Chem Soc., 79, 1636 (1957)], 2.08 g., is dissolved in 80 ml. of dimethylformamide and cooled to −20° C. The solution is treated with 11.25 ml. of 2.66 N hydrogen chloride in tetrahydrofuran and then with 1.04 ml. of 90% isopentyl nitrite. The reaction is stirred at −20° C for 30 minutes, cooled to −25° C and 4.87 ml. of triethylamine added. D-Tryptophyl-L-leucine methyl ester hydrochloride, 2.2 g., is then added and the reaction stirred at −20° C for 30 minutes, at −20° to −10° C. for 30 minutes and at 0° C. for 3 hours. It is then stored at 5° C. for 16 hours, filtered and the solvent removed under reduced pressure. The residue is dissolved in 400 ml. of ethyl acetate and the solution washed with 0.5 N hydrochloric acid, saturated sodium chloride solution, 5% sodium bicarbonate solution and saturated sodium chloride solution. The ethyl acetate solution is dried and the solvent removed to about 50 ml. volume. The solution is refrigerated overnight, filtered and dried to give the above named product 3.3 g.; mp. 110°–113° C.; $[\alpha]_D^{23}$ −25° (c 1.03, methanol).

(d) L-Seryl-L-tyrosyl-D-tryptophyl-L-leucine methyl ester

N$^\alpha$-Benzyloxycarbonyl-L-seryl-L-tyrosyl-D-tryptophyl-L-leucine methyl ester, 9.0 g., is dissolved in 850 ml. of boiling methanol. The solution is shaken with hydrogen and 1200 mg. of 20% palladium-on-carbon at room temperature and atmospheric pressure. The reaction is complete in thirty to forty minutes as shown by thin layer chromatography. The reaction mixture is filtered, the solvent evaporated from the filtrate and the residue dried under reduced pressure, 7.1 g., and is used without purification.

(e) N$^\alpha$-Benzyloxycarbonyl-L-isoleucyl-L-tryptophan methyl ester

N$^\alpha$-Benzyloxycarbonyl-L-isoleucine, 2.65 g., and 2.54 g. of L-tryptophan methyl ester hydrochloride are dissolved in 30 ml. of dimethylformamide and cooled in an ice bath. Triethylamine, 1.4 ml., is added and then 1.5 g. of 1-hydroxy-benzotriazole. Lastly 2.3 g. of dicyclohexylcarbodiimide is added and the reaction let warm to room temperature with stirring continued for 40 hours. The mixture is filtered and the solvent evaporated. The residue is dissolved in 150 ml. of ethyl acetate and washed with 0.5 N hydrochloric acid, saturated sodium chloride solution, 5% sodium bicarbonate solution and finally with saturated sodium chloride solution. The ethyl acetate solution is dried over magnesium sulfate, filtered and the solution evaporated. The product is crystallized from methanol-ether-hexane to give 2.58 g. of the above named product, mp. 152°–155° C; $[\alpha]_D^{23}$ −16.6° (c 1.95, methanol).

(f) N$^\alpha$-Benzyloxycarbonyl-L-isoleucyl-L-tryptophyl hydrazide

N$^\alpha$-Benzyloxycarbonyl-L-isoleucyl-L-tryptophan methyl ester, 2.58 g. is dissolved in 60 ml. of methanol, 3 ml. of hydrazine hydrate added and the reaction let stand at room temperature. After two days, the precipitated solid is separated by filtration and dried to give 2.0 g. of the above named product, mp. 224°–226° C.

(g) N$^\alpha$-Benzyloxycarbonyl-L-isoleucyl-L-tryptophyl-L-seryl-L-tyrosyl-D-tryptophyl-L-leucine methyl ester N$^\alpha$-Benzyloxycarbonyl-L-isoleucyl-L-tryptophyl hydrazide, 3.2 g., is dissolved in 90 ml. of dimethylformamide and cooled to −20° C. The solution is treated with 13.74 ml. of 3.0 N hydrogen chloride in tetrahydrofuran then with 1.5 ml. of 90% isopentyl nitrite and is stirred at −20° C. for 30 minutes. The mixture is cooled to −25° C. and is treated with 5.74 ml. of triethylamine. L-Seryl-L-tyrosyl-D-tryptophyl-L-leucine methyl ester, 4.0 g., is added and the reaction stirred for thirty minutes at −20° C., 30 minutes at −20° to −10° C. and 3 hours at 0° C. It is then stored at 5° C. for 16 hours, filtered and the solvent evaporated under reduced pressure. The residue is suspended in 400 ml. of ethyl acetate and 50 ml. of water with vigorous shaking and is filtered. The solid is suspended in ether, 150 ml., stirred for thirty minutes, filtered, and dried giving the above named product 5.89 g.

(h)

$N^\alpha$-Benzyloxycarbonyl-L-isoleucyl-L-tryptophyl-L-seryl-L-tyrosyl-D-tryptophyl-L-leucyl hydrazide $N^\alpha$-Benzyloxycarbonyl-L-isoleucyl-L-tryptophyl-L-seryl-L-tyrosyl-D-tryptophyl-L-leucine methyl ester, 5.8 g., is dissolved in 50 ml. of dimethylformamide and 5.8 ml. of hydrazine hydrate added. The reaction is let stand at room temperature for three days, diluted with 250 ml. of absolute ethanol and let stand at room temperature for 24 hours and then at 5° C. overnight. The mixture is filtered and the solid triturated with ether and dried to give 5.2 g. of the above named product, mp. 254°–255° C.; $[\alpha]_D^{23}$ −8.7° (c 1.01, DMF).

(i)

$N^\alpha$-Benzyloxycarbonyl-L-isoleucyl-L-tryptophyl-L-seryl-L-tyrosyl-D-tryptophyl-L-leucyl-L-arginyl-L-prolyl-glycinamide $N^\alpha$-Benzyloxycarbonyl-L-isoleucyl-L-tryptophyl-L-seryl-L-tyrosyl-D-tryptophyl-L-leucyl hydrazide, 3.0 g., is dissolved in 80 ml. of dimethylformamide and cooled to −20° C. The solution is treated with 6.96 ml. of 2.5 N hydrogen chloride in tetrahydrofuran and then with 0.62 ml. of 90% isopentyl nitrite. The reaction is stirred at −20° C. for 30 minutes, cooled to −25° C. and treated with 2.47 ml. of triethylamine and then with 1.1 g. of L-arginyl-L-prolyl-glycinamide hydrochloride (example 2, f). The reaction is stirred at −20° C. for 30 minutes, then for 15 minutes at −20° C to −10° C.; 3 hours at 0° C. and finally is stored overnight at 5° C. The mixture is filtered and concentrated under reduced pressure to yield a glass. The crude product is triturated with tetrahydrofuran for twenty hours, the solvent decanted and the solid dissolved in 30 ml. of methanol and added slowly to 250 ml. of ethyl acetate with stirring. The mixture is stored in the cold for two days and is then filtered and the solid product dried under reduced pressure to give 3.37 g. of $N^\alpha$-benzyloxycarbonyl-L-isoleucyl-L-tryptophyl-L-seryl-L-tyrosyl-D-tryptophyl-L-leucyl-L-arginyl-L-prolyl-glycinamide hydrochloride.

The product is purified by chromatography over silica gel in chloroform:methanol:water (60:45:10). The eluted fractions are selected according to thin layer chromatography and are evaporated, the residue taken into methanol, 100 ml., and precipitated in four volumes of ether and the solid separated and dried to yield 1.35 g. This material is converted to the acetic salt by dissolving 1.35 g. of the hydrochloride in 80 ml. of methanol and passing the solution through 65 ml. of Dowex 1×2 resin (acetate form). The eluates are evaporated and the residue taken into water and lyophilized giving 1.22 g. of the acetate of the above named product; $[\alpha]_D^{23}$ −20.4° (c 1.0, DMF).

We claim:

1. A compound having the name $N^\alpha$-Benzyloxycarbonyl-L-leucyl-L-tryptophyl-L-seryl-L-tyrosyl-D-asparaginyl-L-leucyl-arginyl-L-prolyl-glycinamide and salts thereof.

2. A compound having the name $N^\alpha$-t-Butoxycarbonyl-O-benzyl-L-seryl-L-tryptophyl-L-seryl-L-tyrosyl-D-seryl-L-leucyl-L-arginyl-L-prolyl-glycinamide and salts thereof.

3. A compound having the name $N^\alpha$-benzyloxycarbonyl-O-benzyl-L-seryl-L-tryptophyl-L-seryl-L-tyrosyl-D-phenylalanyl-L-leucyl-L-arginyl-L-prolyl-glycinamide and salts thereof.

4. A compound having the name $N^\alpha$-benzyloxycarbonyl-L-glutaminyl-L-tryptophyl-L-seryl-L-tyrosyl-D-phenylalanyl-L-leucyl-L-arginyl-L-prolyl-glycinamide and salts thereof.

5. A compound having the name $N^\alpha$-t-butoxycarbonyl-O-benzyl-L-seryl-L-tryptophyl-L-seryl-L-tyrosyl-D-tryptophyl-L-leucyl-L-arginyl-L-prolyl-glycinamide and salts thereof.

6. A compound having the name $N^\alpha$-benzyloxycarbonyl-L-glutaminyl-L-tryptophyl-L-seryl-L-tyrosyl-D-tryptophyl-L-leucyl-L-arginyl-L-prolyl-glycinamide and salts thereof.

7. A compound having the name $N^\alpha$-benzyloxycarbonyl-O-benzyl-L-tyrosyl-L-tryptophyl-L-seryl-L-tyrosyl-D-leucyl-L-leucyl-L-larginyl-L-prolylglycinamide and salts thereof.

8. A compound having the name $N^\alpha$-benzyloxycarbonyl-L-isoleucyl-L-tryptophyl-L-seryl-L-tyrosyl-D-tryptophyl-L-leucyl-L-arginyl-L-prolyl-glycinamide and salts thereof.

9. A compound having the name $N^\alpha$-p-methoxybenzyloxycarbonyl-O-benzyl-L-seryl-L-tryptophyl-L-seryl-L-tyrosyl-D-phenylalanyl-L-leucyl-L-arginyl-L-prolyl-glycinamide hydrochloride and salts thereof.

* * * * *